(12) United States Patent
Chen et al.

(10) Patent No.: US 10,661,095 B2
(45) Date of Patent: May 26, 2020

(54) PHOTODYNAMIC THERAPY FOR USE IN TREATING CANCER

(71) Applicant: THE BOARD OF REGENTS, THE UNIVERSITY OF TEXAS SYSTEM, Austin, TX (US)

(72) Inventors: Wei Chen, Arlington, TX (US); Lun Ma, Arlington, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/745,105

(22) PCT Filed: Aug. 25, 2016

(86) PCT No.: PCT/US2016/048564
§ 371 (c)(1),
(2) Date: Jan. 15, 2018

(87) PCT Pub. No.: WO2017/035309
PCT Pub. Date: Mar. 2, 2017

(65) Prior Publication Data
US 2019/0015678 A1    Jan. 17, 2019

Related U.S. Application Data

(60) Provisional application No. 62/210,137, filed on Aug. 26, 2015.

(51) Int. Cl.
*A61N 5/02* (2006.01)
*A61K 9/00* (2006.01)
*A61K 9/51* (2006.01)
*A61K 33/34* (2006.01)
*A61N 5/06* (2006.01)

(52) U.S. Cl.
CPC ............ *A61N 5/062* (2013.01); *A61K 9/0009* (2013.01); *A61K 9/5115* (2013.01); *A61K 33/34* (2013.01); *A61N 5/022* (2013.01)

(58) Field of Classification Search
None
See application file for complete search history.

(56) References Cited

U.S. PATENT DOCUMENTS 5,257,970 A * 11/1993 Dougherty ............. A61K 9/127
424/450

OTHER PUBLICATIONS

Casciato et al. Manual of Clinical Oncology 6th edition. 2009. Lippincott Williams & Wilkins:Philadelphia p. ix (Year: 2009).*
Mak et al. American Journal of Translational Research 2014 6(2):114-118 (Year: 2014).*
Wen et al. Lasers in Medical Science 2012 27:445-452 (Year: 2012).*
Ma et al. Journal of Biomedical Nanotechnology 2014 10:1501-1508 (Year: 2014).*
Ma et al. Journal of Materials Chemistry C 2014 2:4239-4246 (Year: 2014).*

* cited by examiner

*Primary Examiner* — Robert A Wax
*Assistant Examiner* — Caralynne E Helm
(74) *Attorney, Agent, or Firm* — FisherBroyles LLP; Anthony Dovale

(57) ABSTRACT

Disclosed is the use of copper cysteamine nanoparticles for use in photodynamic cancer therapy. The disclosed methods of treatment utilize microwave radiation as a means for activating the copper cysteamine photosensitizer.

7 Claims, 34 Drawing Sheets

PHOTODYNAMIC THERAPY FOR USE IN TREATING CANCER

CROSS REFERENCE TO RELATED APPLICATIONS

This application is a U.S. National Stage Entry of International Application No. PCT/US16/48564 filed Aug. 25, 2016, which claims the benefit of Provisional Application Ser. No. 62/210,137, filed on Aug. 26, 2015, the entire disclosure of which are incorporated herein by reference in their entirety.

FIELD

Disclosed is the use of copper cysteamine (Cu-Cy) nanoparticles for use in photodynamic cancer therapy. The disclosed methods of treatment utilize microwave radiation as a means for activating the copper cysteamine photosensitizer.

BRIEF DESCRIPTION OF THE FIGURES

FIGS. 2A-2C are control groups; 2A sample was not irradiated, 2B was irradiated at 20 W for 5 minutes and 2C was irradiated at 20 W for 10 minutes. FIG. 2D and FIG. 2E are cells treated with 6.25 μg/mL of Cu-Cy nanoparticles. The cells in FIG. 2D were not irradiated. The cells in FIG. 2E were irradiated at 20 W for 5 minutes. FIG. 2F represents cells treated with 25 μg/mL of Cu-Cy nanoparticles and irradiated for 10 minutes at 20 W. FIG. 2G represents cells treated with 25 μg/mL of Cu-Cy nanoparticles that were not irradiated. FIG. 2H represents cells treated with 25 μg/mL of Cu-Cy nanoparticles that were irradiated for 5 minutes at 20 W. FIG. 2I represents cells treated with 25 μg/mL of Cu-Cy nanoparticles that were irradiated for 10 minutes at 20 W. Scale bar is 100 μm.

FIG. 6 depicts the tumor growth curves for the various animal groups.

FIG. 9A is the control wherein Cu-Cy is absent, FIG. 9B represents tumors with 25 µg/mL of Cu-Cy and FIG. 9C represents tumors with 100 µg/mL of Cu-Cy. The arrows assist in identifying Cu-Cy nanoparticles.

FIG. 10A is visualization of tumor cells treated with 25 mg/mL Cu-Cy and irradiated with microwave radiation. FIG. 10B is visualization of tumor cells treated with 6.25 mg/mL Cu-Cy and irradiated with microwave radiation. FIG. 10C is visualization of tumor cells treated with saline and irradiated with microwave radiation. FIG. 10D is visualization of tumor cells treated with 25 mg/mL Cu-Cy and irradiated with ultra violet radiation. FIG. 10E is visualization of tumor cells treated with 6.25 mg/mL Cu-Cy and irradiated with ultra violet radiation. FIG. 10F is visualization of tumor cells treated with saline and irradiated with ultraviolet radiation. FIG. 10G is visualization of tumor cells treated with 25 mg/mL Cu-Cy without radiation. FIG. 10H is visualization of tumor cells treated with 6.25 mg/mL Cu-Cy without radiation. FIG. 10I is visualization of tumor cells treated with saline without radiation.

FIG. 11A represents cells treated with 25 µg/mL Cu-Cy that were not irradiated. FIG. 11B represents cells treated with 6.25m/mL Cu-Cy that were not irradiated. FIG. 11C are control cells not irradiated. FIG. 11D represents cells treated with 25 µg/mL Cu-Cy that were treated with 20 W for 5 minutes. FIG. 11E represents cells treated with 6.25m/mL Cu-Cy that were treated with 20 W for 5 minutes. FIG. 11F are control cells that were treated with 20 W for 5 minutes.

FIG. 12A represents cell treated with 0 (black), 6.25m/mL (hatched) and 25 µg/mL (white) of Cu-Cy without irradiation. FIG. 12B represents cell treated with 0 (black), 6.25 µg/mL (hatched) and 25 µg/mL (white) of Cu-Cy that were irradiated with 20 W of microwave radiation for 5 minutes.

FIG. 23A is the spectrum obtained from a control sample containing no Cu-Cy nanoparticles. FIG. 23B and FIG. 23C are cells treated with 6.25 µg/mL and 25 µg/mL respectively. FIG. 23D is the spectrum of irradiated cells containing no Cu-Cy nanoparticles. FIG. 23E and FIG. 23F are cells treated with 6.25 µg/mL and 25 µg/mL respectively then irradiated with 20 W microwave energy for 5 minutes.

DETAILED DESCRIPTION

Figure 1A:
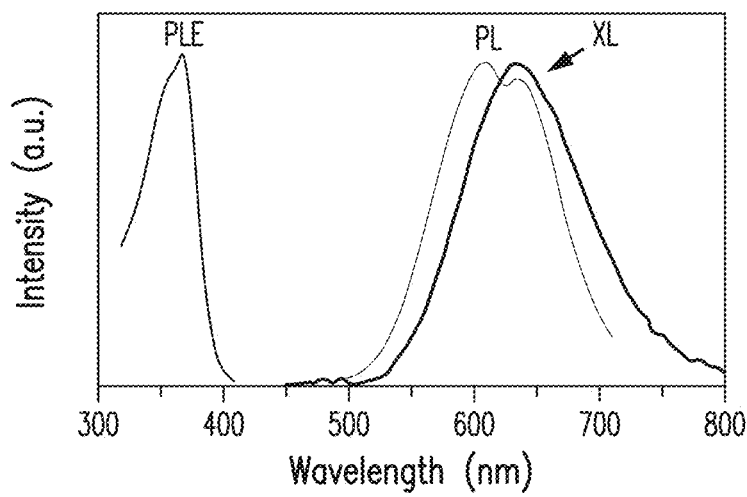
FIG. 1A depicts the photoluminescence excitation (PLE) and emission at 650 nm, photoluminescence emission (PL) (excitation at 360 nm) and X-Ray excited luminescence (XL) of the disclosed copper cysteamine (Cu-Cy) particles.

The materials, compounds, compositions, articles, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

The terms "a" and "an" are defined as one or more unless this disclosure explicitly requires otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Values expressed as "greater than" do not include the lower value. For example, when the "variable x" is defined as "greater than zero" expressed as "0<x" the value of x is any value, fractional or otherwise that is greater than zero.

Similarly, values expressed as "less than" do not include the upper value. For example, when the "variable x" is defined as "less than 2" expressed as "x<2" the value of x is any value, fractional or otherwise that is less than 2.

"Optional" or "optionally" means that the subsequently described event or circumstance can or cannot occur, and that the description includes instances where the event or circumstance occurs and instances where it does not.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps. The term "photodynamic therapy" (PDT) refers to phototherapy and photochemotherapy in which photosensitizers (PSs) are used to generate highly reactive oxygen species (ROS) by means of photoexcitation, such as hydroxyl radicals (.OH), singlet oxygen ($^1O_2$), as well as peroxides (R—O—O.) which irreversibly damage a target of interest, for example, cancer cells. (See, Fang J. et al., "Therapeutic Strategies by Modulating Oxygen Stress in Cancer and Inflammation," *Adv Drug Delivery Rev* 2009; 61:290-302, Kehrer J P, "Free Radicals as Mediators of Tissue Injury and Disease," *Chem Rev Toxicol* 1993; 23:21-48 and Wang S. et al, "Plasmonic Copper Sulfide Nanocrystals Exhibiting Near-Infrared Photothermal and Photodynamic Therapeutic Effects," *ACS Nano* 2015; 9 (2): 1788-800.)

The term "microwave radiation" refers to electromagnetic radiation having a wavelength from about 1 nanometer to about 1 meter and/or a frequency of from about 300 gigaHertz (GHz) to about 1 GHz.

The term "contacting cells" refers to the exposing to target cells a composition comprising the disclosed Cu-Cy nanoparticles such that the nanoparticles are taken up, absorbed or otherwise become entrained in the target cell such that when the target cell area is exposed to microwave radiation, the result is cell death either to the cell which contains the Cu-Cy nanoparticles or nearby cells which are damaged by the reactive oxygen species formed. In the case of tumors, Cu-Cy nanoparticles which remain in the interstices between cells will also produce reactive oxygen species and thereby contribute to the target cell death.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

Any embodiment of any of the disclosed methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are described below.

Disclosed herein are photodynamic methods for the treatment of cancer. The disclosed methods comprise contacting cancer cells, especially in the form of tumors, with copper-cysteamine (Cu-Cy) nanoparticles and applying microwave radiation to the nanoparticles. Without wishing to be limited by theory, the irradiated Cu-Cy nanoparticles generate highly reactive oxygen species (ROS) by means of photo-excitation, such as hydroxyl radicals (.OH), singlet oxygen ($^1O_2$), as well as peroxides (R—O—O.) which irreversibly damage a target of interest, for example, cancer cells.

In one aspect the disclosed photodynamic therapies comprise:
a) contacting cancer cells with copper-cysteamine; and
b) exposing the copper-cysteamine with a source of microwave radiation.

In another aspect the disclosed photodynamic therapies comprise:
a) contacting target cells with copper-cysteamine; and
b) exposing the copper-cysteamine with a source of microwave radiation.

For the purposes of the present disclosure the term "exposing" means irradiation of cells with a source of microwave radiation. Exposing to cells is used interchangeably with "treating cells", "killing cells" and the like. Cells that have taken up the disclosed Cu-Cy nanoparticles when exposed to microwave radiation form reactive oxygen species which are capable of inducing cell death.

Disclosed herein is the use of copper-cysteamine (Cu-Cy) nanoparticles for the treatment of cancer. Cu-Cy has the formula:

$$Cu_3Cl(SR)_2$$

wherein R is —$CH_2CH_2NH_2$. The terms "copper-cysteamine," "Cu-Cy material," "Cu-Cy complex," "Cu-Cy," "disclosed material," "disclosed complex," "disclosed compound" and the like are used herein interchangeably throughout the present disclosure to represent the above-identified chemical compound. As depicted in the appended Figures, the compound can have various forms depending upon the method of preparation employed by the formulator. The present disclosure does not exclude any morphology, crystalline form and the like.

The disclosed complex Cu-Cy nanoparticles exhibit an emission peak at 607 nm and 633 nm and X-ray luminescence at 633 nm. The Cu-Cy materials are stable in aqueous solution, as well as other common solvents. FIG. 1A shows the photoluminescence excitation (PLE), emission (PL) and X-ray excited luminescence (XL) spectra of Cu-Cy nanoparticles. The insets in FIG. 1A are photos of the Cu-Cy aqueous solution under room light (a) and excited by a UV lamp (b).

Figure 21:
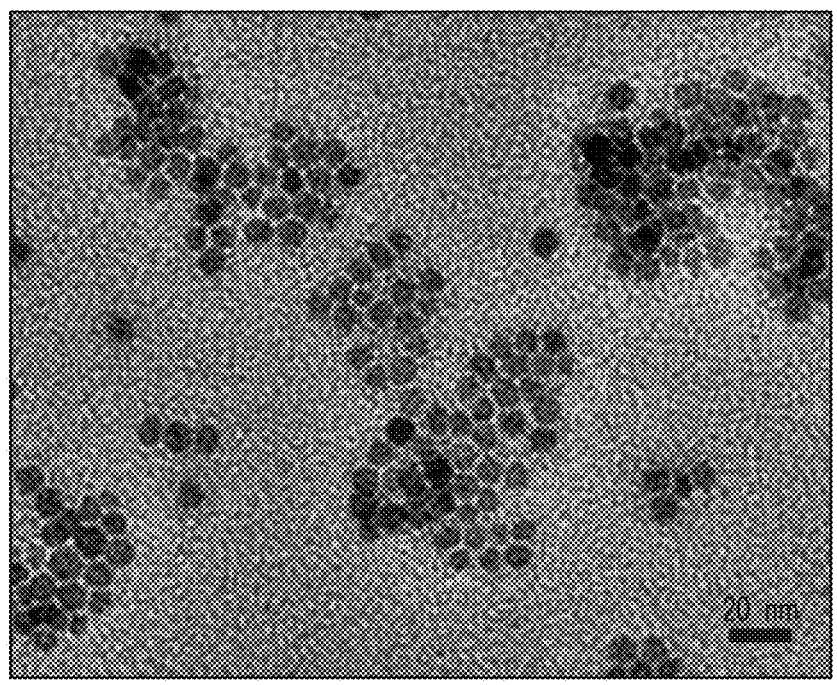
FIG. 21 is a Transmission electron microscope (TEM) image of the disclosed Cu-Cy nanoparticles. As indicated by the reference bar, the average size is approximately 15 nm.

The disclosed Cu-Cy materials can be formed in crystals in micrometer or millimeter size. In addition to the micron-sized crystals, smaller crystals from tens to several hundred nanometers have also been prepared. The methods for producing the copper-complex materials can be accomplished without the protection afforded by an inert atmosphere, for example, nitrogen or argon blanketing or the need for hazardous organic solvents. After simply mixing and heating the copper and organic reactants in water, the Cu-Cy crystals are formed and isolated from water solution as precipitation. The product can be then washed with water and ethanol as more specifically described in the examples. Sonication helps cleaning the products but is likely to break the crystals into small pieces. The particle size of the nanoparticles used for the testing described herein below is about 15 nm as determined by transmission electron microscope shown in FIG. 21.

The disclosed Cu-Cy nanoparticles can be prepared as follows. $CuCl_2.2H_2O$ (0.460 g, 2.698 mmol) is dissolved in deionized distilled water followed by addition of cysteamine (0.636 g, 8.244 mmol). The pH is adjusted to approximately 8 by the addition of 2.5 M NaOH (8 mL) after which the solution is stirred for about 2 hours at room temperature The solution is then heated to boiling for 30 minutes. Particles of Cu-Cy are obtained by centrifuging and washing the crude product with a solution of DI water and ethanol (v/v=5:4) three times followed by sufficient sonication. The particles are dried completely in a vacuum oven at room temperature overnight.

Without wishing to be limited by theory, the overall reaction to prepare the desired copper-cysteamine complex is as follows:

$$6CuCl_2+12\ HSR+12\ NaOH \rightarrow 2\ Cu_3Cl(SR)_2+3\ RSSR+2\ Na(SR)+10\ NaCl+12H_2O$$

wherein R is —$CH_2CH_2NH_2$.

Procedures

Photoluminescence and X-Ray Excited Luminescence Measurement

The photoluminescence spectrum, FIG. 1A, of the disclosed Cu-Cy nanoparticles was measured by dispersing 0.1 mg Cu-Cy particles into 3 mL DI water and using a Shimadzu RF-5301PC fluorescence spectrophotometer (Kyoto, Japan). The X-ray excited luminescence was measured by a Faxitron RX-650 (Faxitron X-ray Corp, IL, USA) at 90 kV as the radiation source. The spectrum was recorded by using a QE65000 spectrometer (Ocean Optics Inc. FL, USA) connected to the X-ray chamber using a 0.6 mm core diameter optic fiber (P600-2-UV-V is, Ocean Optics Inc., FL, USA), which has a probe head extended inside the x-ray chamber and positioned at 45° and 5 mm away from sample surface.

Cell Culture and Nanoparticle Uptake Cellular Uptake

Figure 9:
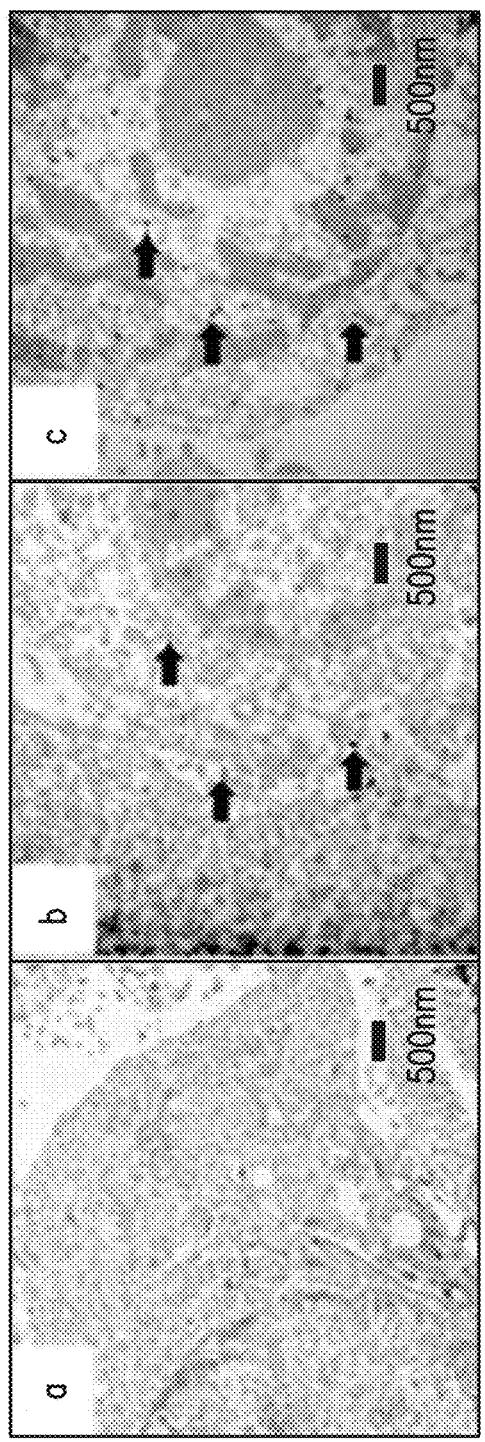
FIGS. 9A-9C are transmission electron microscopy (TEM) images of Cu-Cy in various concentrations in UMR-106 cells.

Rat osteosarcoma UMR-106 cells (ATCC CRL-1661) were cultured in Dulbecco's Modified Eagle's Medium (DMEM, Gibco, USA) supplemented with 10% fetal bovine serum (FBS, Sciencell, USA) and containing 100 U/mL penicillin and 100 μg/mL streptomycin. The cells were seeded in a 6-well plate at a density of $1 \times 10^6$ cells/mL and incubated for 24 hours at 37° C. in a humidified atmosphere of 5% v/v $CO_2$. After removing the culture medium, different concentrations (0, 25 and 100 μg/mL) of Cu-Cy nanoparticle solutions were added to the 6-well plate, at 2 mL per well. After incubation for 24 hours, the cells were detached by trypsinization (0.25% trypsin in Ethylenediaminetetraacetic acid (EDTA)) and concentrated by centrifugation at 1,000 rpm for 5 min. Then, the cell sample was fixed in 3% glutaraldehyde for 24 hours, washed with phosphate-buffered saline (PBS) three times and fixed again with 1% osmium tetroxide for 2 hours. The cells were dehydrated via sequential treatment with 30, 50, 70, 80, 90, and 100% ethyl alcohol for 10 minutes each. The fixed cells were embedded with Epon812, and small blocks of cells in the Epon812 were cut with an ultramicrotome (Leica Ultracut, Germany). The ultrathin sections were then positively stained with uranylacetate and lead citrate. The nanoparticle uptake in the cells was observed using a transmission electron microscope (H-7650, HITACHI, Japan). The results are shown in FIGS. 9A-C. FIG. 9A is the control without Cu-Cy as a reference. FIGS. 9B and 9C display images of tumors treated with 25 and 100 μg/mL of Cu-Cy respectively. The arrows assist in identifying Cu-Cy nanoparticles. The reference bars are 500 nm.

Cytotoxicity Studies of Cu-Cy Nanoparticles Using UMR-106 Cells

Figure 26A:
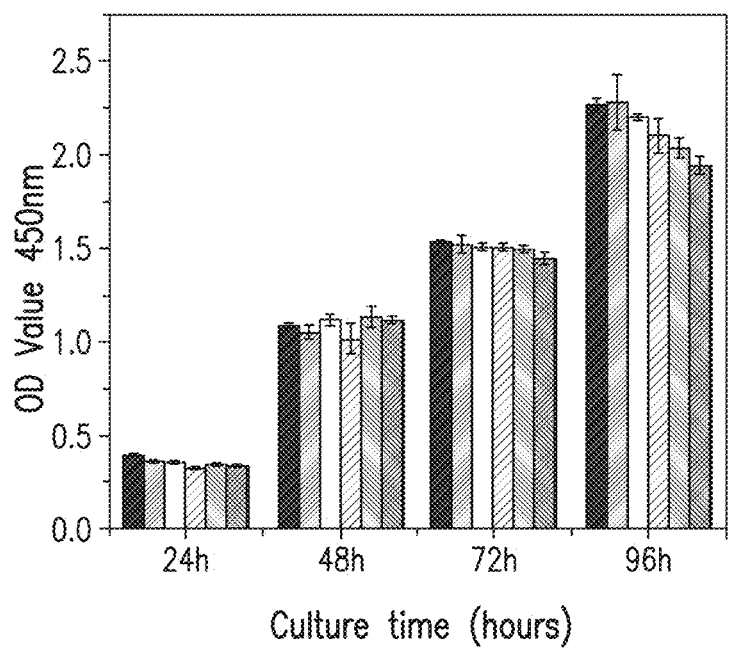
FIG. 26A depicts the cytotoxicity of Cu-Cy solutions on UMR-106 cells as measured by the 3-(4,5-dimethylthiazol-2-yl)-2,5-dimethyltetrazolium bromide (MTT) assay. Reading the bars from left to right the samples were incubated with the following concentrations: reading from left to right, 0 µg/mL Cu-Cy (control), 5 µg/mL Cu-Cy, 10 µg/mL Cu-Cy, 15 µg/mL Cu-Cy, 20 µg/mL Cu-Cy, and 25 µg/mL Cu-Cy over 24, 48, 72 and 96 hours.
Figure 26B:
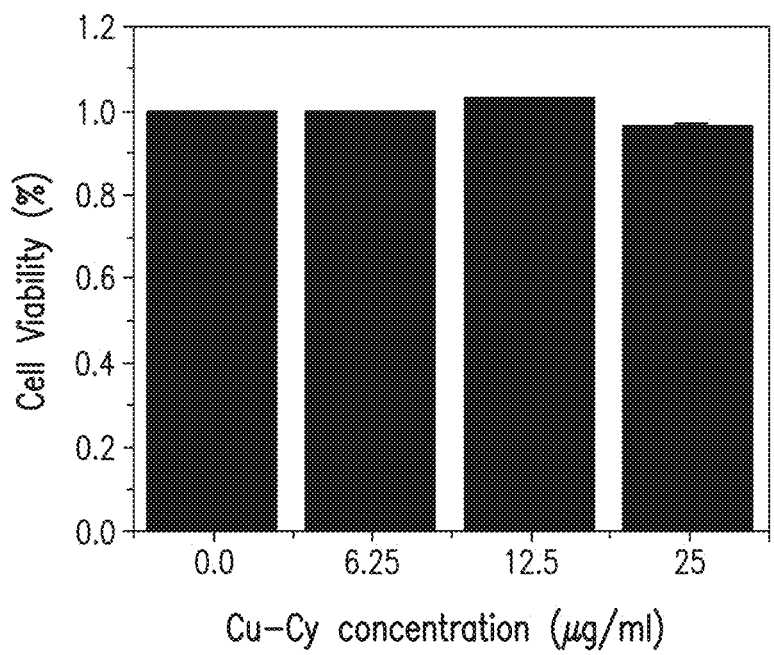
FIG. 26B represents the percent cell viability versus control and 6.25 µg/mL Cu-Cy, 12.5 µg/mL Cu-Cy, and 25 µg/mL Cu-Cy. These results indicate that Cu-Cy nanoparticles have a very low dark (non-irradiated) cytotoxicity for the concentrations listed.
Figure 27:
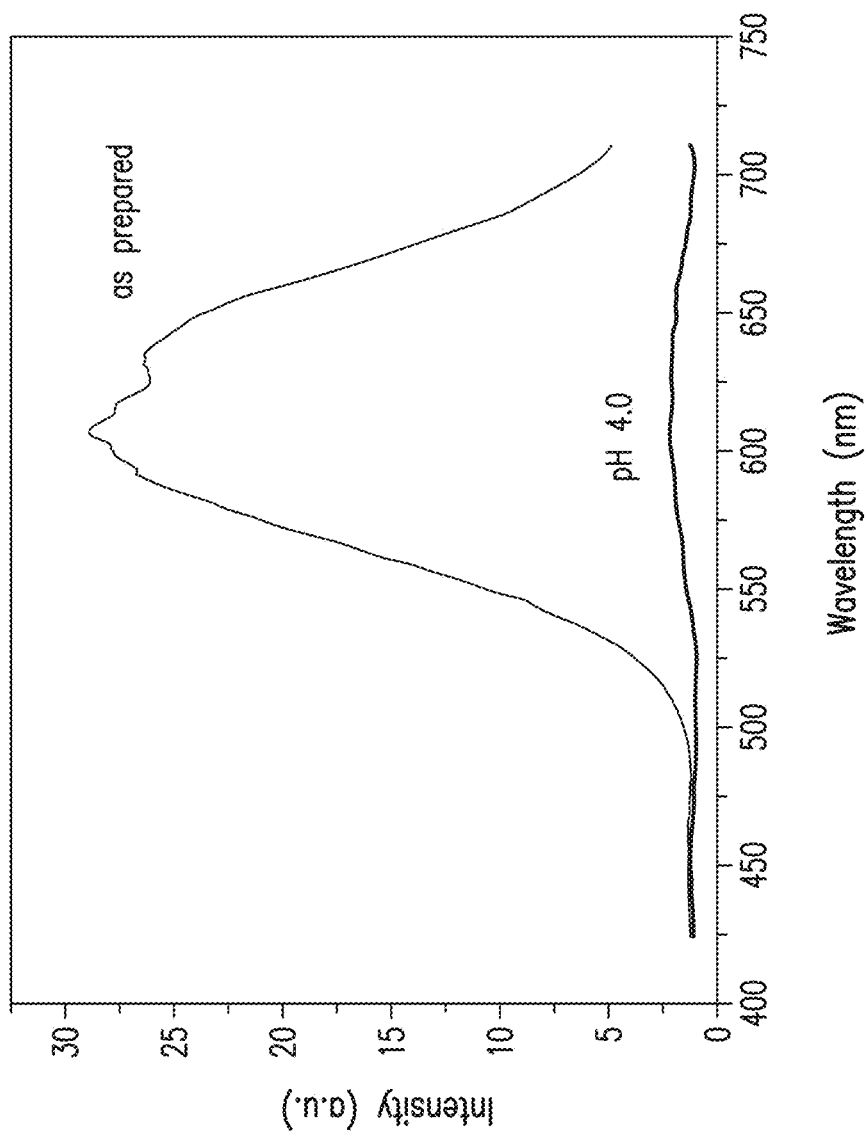
FIG. 27 is the luminescence spectra of Cu-Cy particles for the original particles as prepared and after acid (HCl, volume 10% in DI water, pH=4) treatment at for 5 hours. The excitation is at 360 nm.
Figure 28:
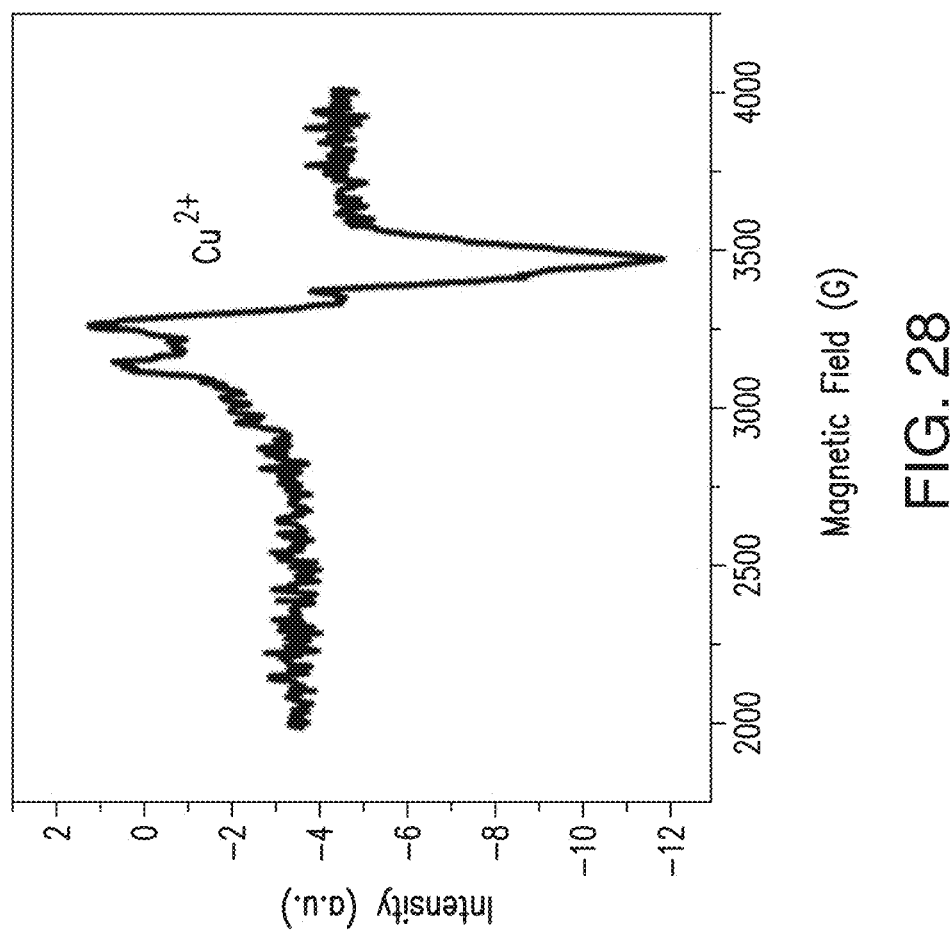
FIG. 28 is the ESR spectrum of Cu-Cy at pH of 4.0 indicating the conversion of $Cu^+$ to $Cu^{2+}$.
Figure 29:
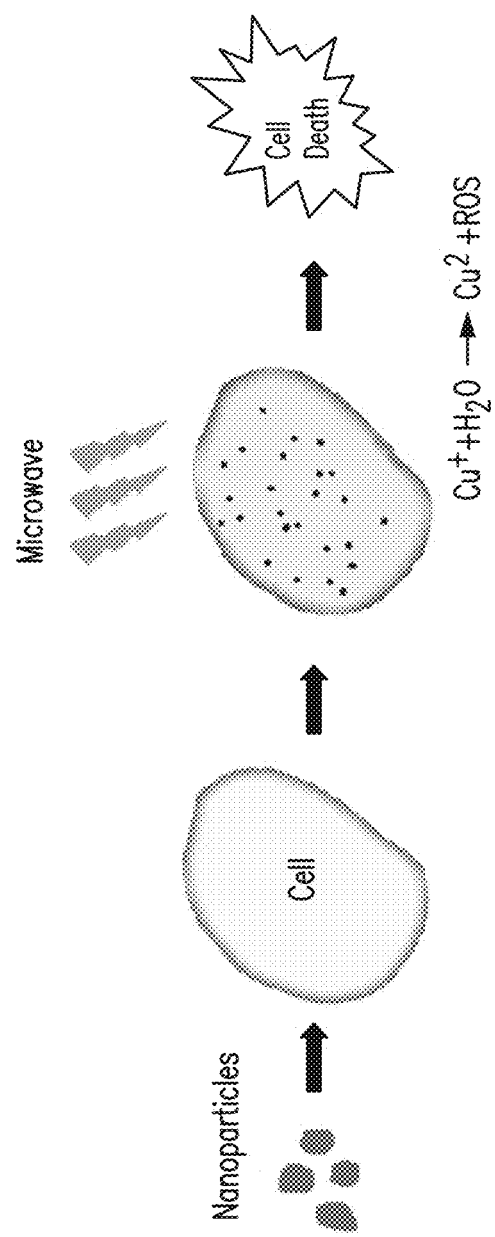
FIG. 29 is a schematic illustration of the disclosed method for treating cancer with the disclosed Cu-Cy using microwave induced formation of reactive oxygen species.

The cell suspension (100 μL) was seeded into a 96-well cell culture plate at a density of $2\times10^4$ cells/mL. The culture medium was removed after 24 hours, and then different concentrations (0, 6.25, 12.5, 25, 50, 100, 200 and 400 μg/mL) of Cu-Cy nanoparticle solutions were added to the plate at 100 μL per well. Cell cytotoxicity was measured using a Cell Counting Kit-8 (CCK-8, Dojindo, Japan). For CCK-8 assay, at each of the designated time points (24, 48 and 72 h), the culture medium was removed, 10 μL of CCK-8 solution and 90 μL DMEM were added to each well of the plate, and the cytotoxicity was evaluated after 4 hours of cell incubation. The optical density of the formazan solution was recorded using a microplate reader (Thermo, Multiskn Go) at 450 nm, and all samples were measured at the same conditions. The results of this procedure are depicted in FIGS. 26A and 26B.

Singlet Oxygen Measurement

1. Aqueous Solution

For singlet oxygen measurement in aqueous solutions, the RNO-ID (p-nitrosodimethyl-aniline (RNO)-imidazole (ID)) method was used as described in literature. (See, Kraljić I et al., "A New Method for the Detection of Singlet Oxygen in Aqueous Solutions," *Photochemistry and Photobiology* 1978; 28(4-5):577-81) RNO (0.225 mg) (Sigma, USA) and ID (16.34 mg) (Sigma, USA) were added to 30 mL deionized (DI) water, which was air saturated by sufficient air bubbling. Sample solutions were prepared by adding 1.5 mg of testing sample (Cu-Cy) into 3 mL (0.5 mg/mL) of the above RNO-ID solution. Then, the RNO-ID solution and sample solutions were exposed to microwaves (MW) for 5 min with various powers of output (0-30 W) using a microwave therapy apparatus (WB-3100A1, BXING, China). A second group of RNO-ID sample solutions were exposed MW at 20 W for various time durations (0-30 min). The intensity of the RNO absorption peak at 440 nm was monitored using a microplate reader (Thermo, Multiskn Go) as a measurement for singlet oxygen concentration.

Figure 1B:
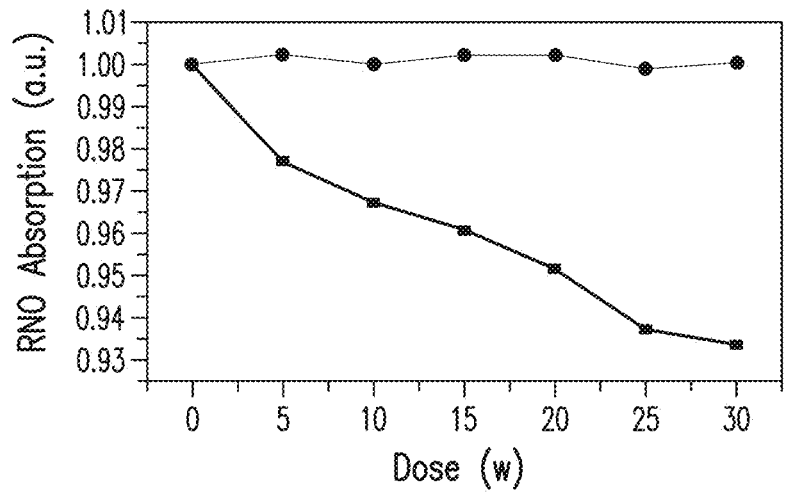
FIG. 1B depicts the relative drop in absorption (quenching) of a p-nitrosodi-methylaniline-imidazole (RNO-ID) solution due to the production of single oxygen at various excitation energies for a 0.5 mg/mL sample of Cu-Cy (■) versus control (●) wherein the samples are irradiated for 5 minutes.

RNO is a water soluble molecule with absorption that can be quenched irreversibly by singlet oxygen in the presence of ID. By comparing the relative quenching of RNO absorption with and without Cu-Cy nanoparticles under microwave irradiation, we have observed singlet oxygen generated by the Cu-Cy nanoparticles with different microwave doses. As shown in FIG. 1B, in the control of RNO-ID, the microwave irradiation did not induce any singlet oxygen to quench the RNO absorption. Cu-Cy nanoparticles, however, continuously quenched the RNO absorption as a function of microwave dose, indicating a continuous generation of singlet oxygen. FIG. 1B depicts the relative drop in absorption (quenching) of the p-nitrosodi-methylaniline-imidazole (RNO-ID) solutions due to the production of single oxygen at various excitation energies for a 0.5 mg/mL sample of Cu-Cy (■) versus control (●) wherein the samples are irradiated for 5 minutes.

Figure 1C:
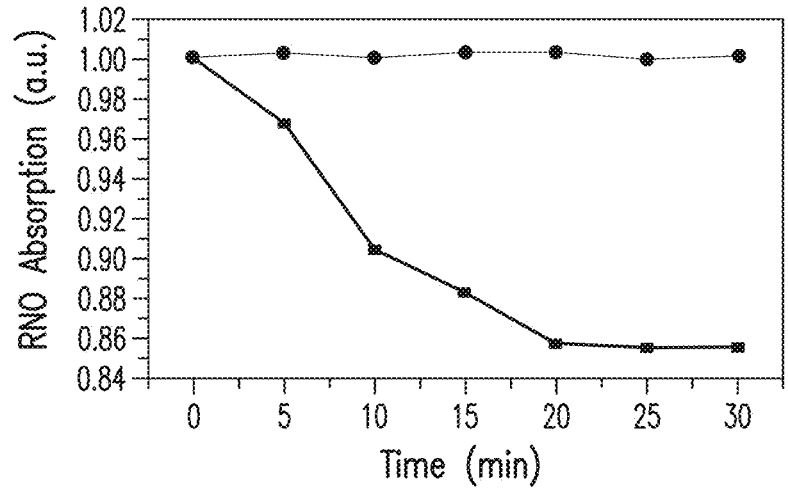
FIG. 1C depicts the relative drop in absorption (quenching) of a p-nitrosodi-methylaniline-imidazole (RNO-ID) solution due to the production of single oxygen when a 0.5 mg/mL sample of Cu-Cy is irradiated at 20 watts (W) for various time lengths (■) versus control (●).

Singlet oxygen production by Cu-Cy nanoparticles were irradiated by MW at 20 W for various time durations was also measured, as shown in FIG. 1C. The results showed that the RNO absorption was quenched continuously with the increasing time of microwave irradiation, which means more singlet oxygen was produced as the microwave irradiation time increased. FIG. 1C depicts the relative drop in absorption (quenching) of the p-nitrosodi-methylaniline-imidazole (RNO-ID) solution due to the production of single oxygen when a 0.5 mg/mL sample of Cu-Cy is irradiated at 20 watts (W) for various time lengths (■) versus control (●).

Figure 22:
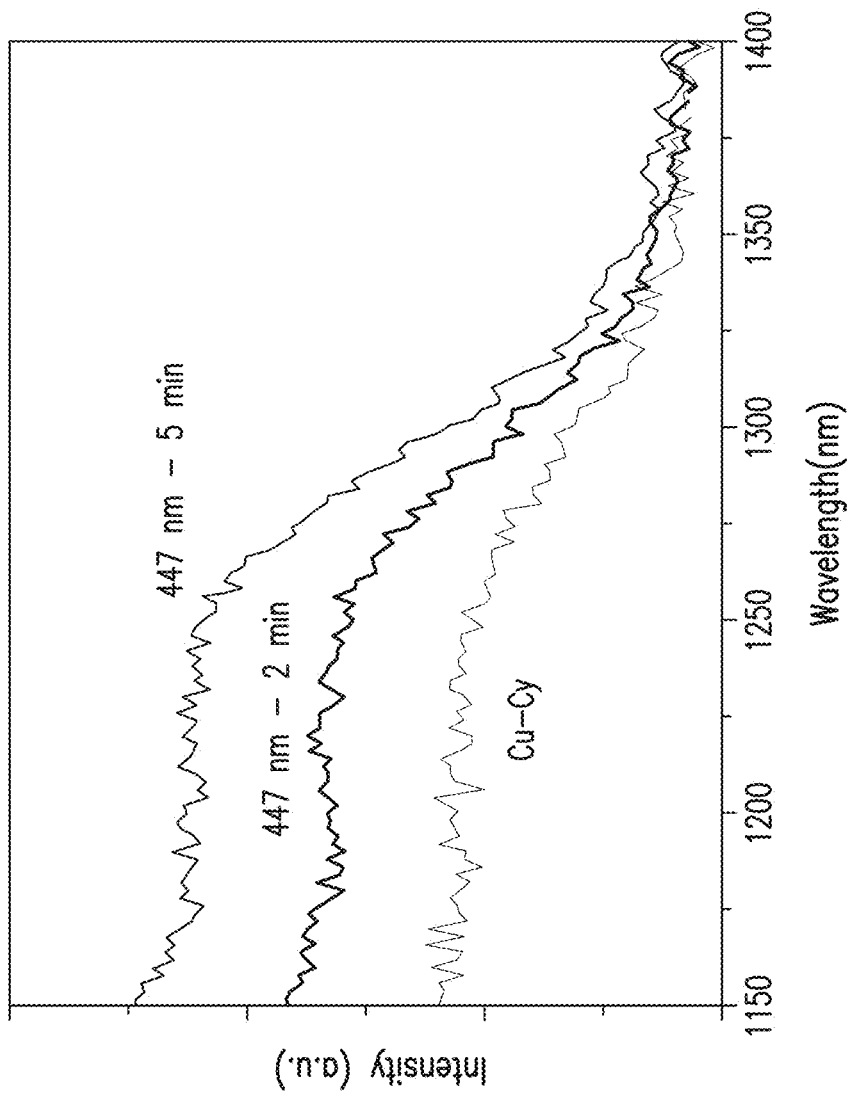
FIG. 22 is the emission spectra of singlet oxygen produced in a Cu-Cy nanoparticle aqueous solution. The bottom line represents an aqueous solution containing 25 µg/mL of Cu-Cy nanoparticles. The middle line represents an aqueous solution containing 25 µg/mL of Cu-Cy nanoparticles that were irradiated at 447 nm for 2 minutes. The yellow line top line represents an aqueous solution containing 25 µg/mL of Cu-Cy nanoparticles that were irradiated at 447 nm for 5 minutes.

In order to confirm that the reactive oxygen species produced by Cu-Cys are singlet oxygen, we measured the 1270 nm luminescence of singlet oxygen, as shown in FIG. 22. Upon irradiation at 447 nm, a broad emission is observed at 1270 nm and the emission increases as the irradiation time is increased. This indicates that the reactive oxygen species produced in Cu-Cy aqueous solutions is singlet oxygen.

2. Singlet Oxygen Detection in UMR-106 Cells

The intracellular singlet oxygen in UMR-106 cells was measured using 2',7'-dichlorodihydrofluorescin diacetate (DCFH-DA, Sigma, USA). (30-33) DCFH-DA passively enters the cell where it reacts with singlet oxygen to form the highly fluorescent compound dichlorofluorescein (DCF). DCFH-DA (0.1M) stock solution (in methanol) was diluted 5,000-fold in DMEM without serum or other additive to yield a 20 μM working solution. The UMR-106 cell suspension (400 μL) was seeded into three 24-well cell culture plates (A, B, and C) at a density of $2\times10^4$ cells/mL. Then the cell suspensions were incubated in a humidified 5% $CO_2$ atmosphere at 37° C. for 24 h. Different concentrations (0, 6.25, and 25 μg/mL) of Cu-Cy nanoparticle solution were added to the plates at 400 μL per well. After incubation for 24 h, the cells in the 24-well plates were washed twice with PBS, incubated in 400 μL solution of DCFH-DA at 37° C. for 30 min and washed gently three times with PBS. Then, 400 μL of DMEM was added into the plates. Culture plate A was exposed to MW at a dose of 20 W for 5 minutes. Culture plate B was exposed to UV light at a dose of 10 mW/cm² for 30 minutes. Plate C was a control without any treatment. The fluorescence intensity of the cells was then visualized with a fluorescence microscope (Olympus BX51, Japan) to measure singlet oxygen produced within the cells.

Figure 10:
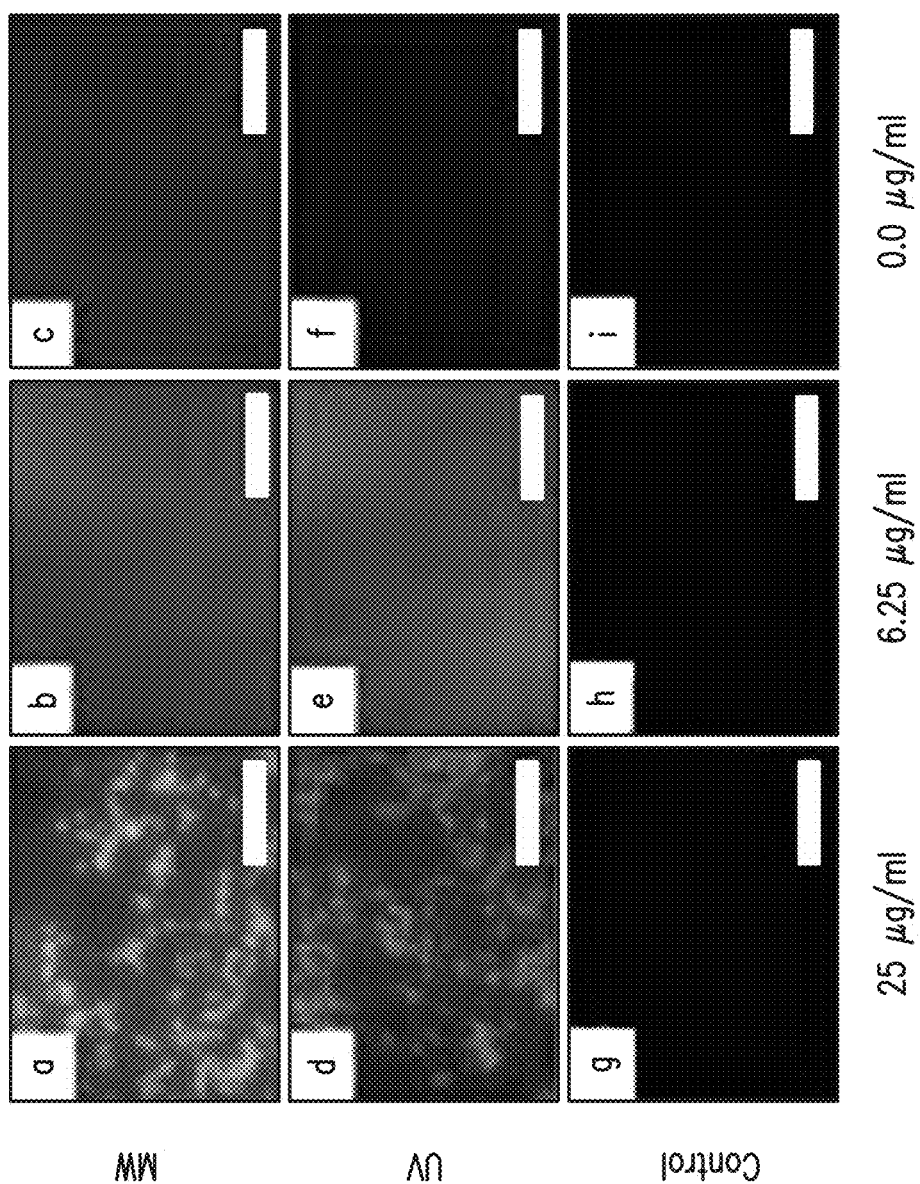
FIGS. 10A-10I represent fluorescent visualizations of singlet oxygen in UMR-106 cells.
Figure 11A:
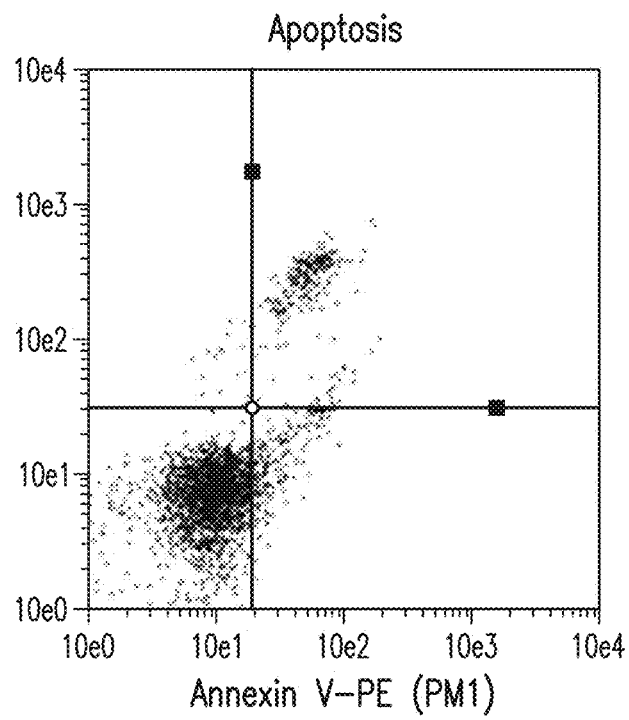
FIGS. 11A-11F depict the apoptosis and necrosis of UMR-106 cell as analyzed by Flow Cytometry.
Figure 11B:
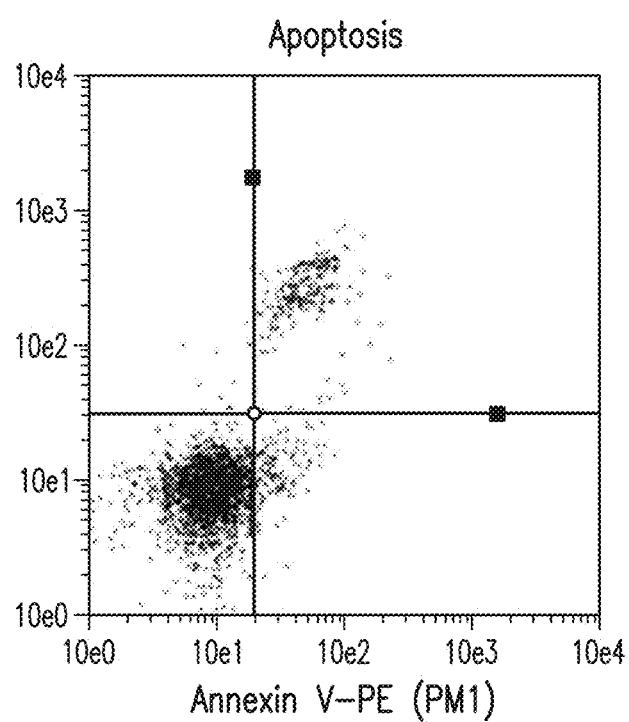
Figure 11C:
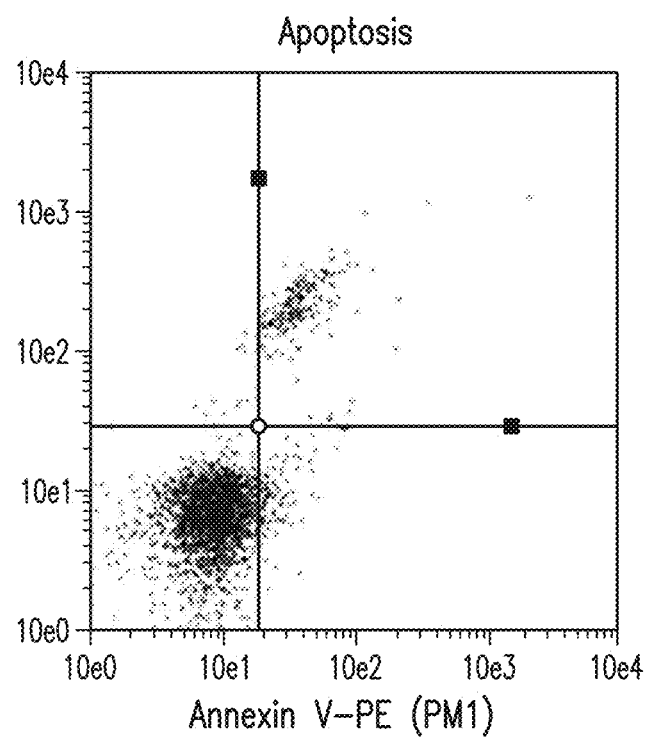
Figure 11D:
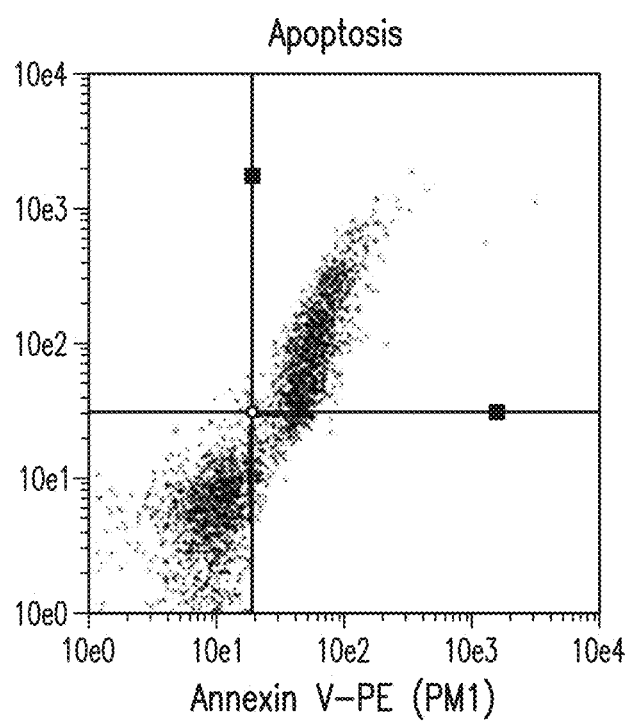
Figure 11E:
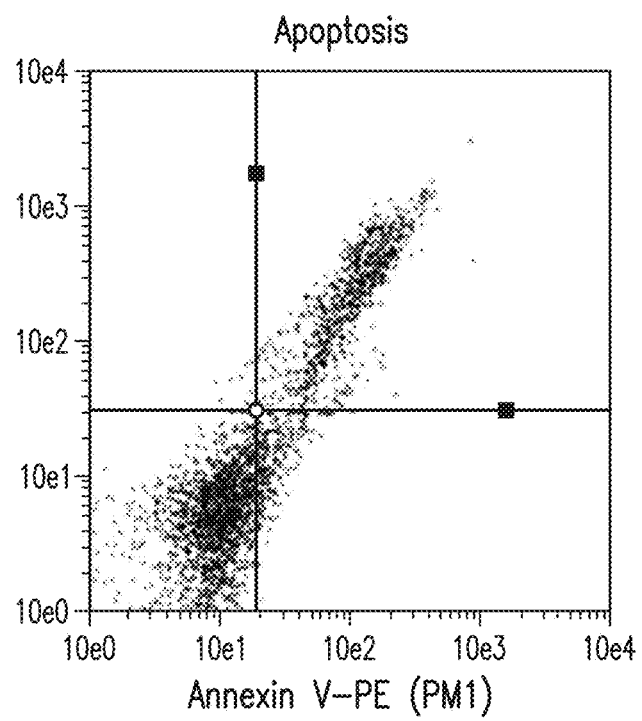
Figure 11F:
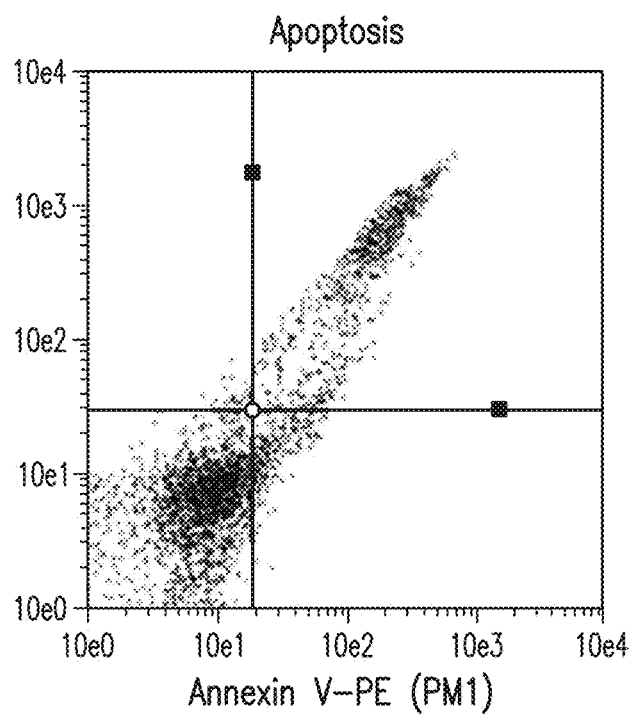
Figure 12A:
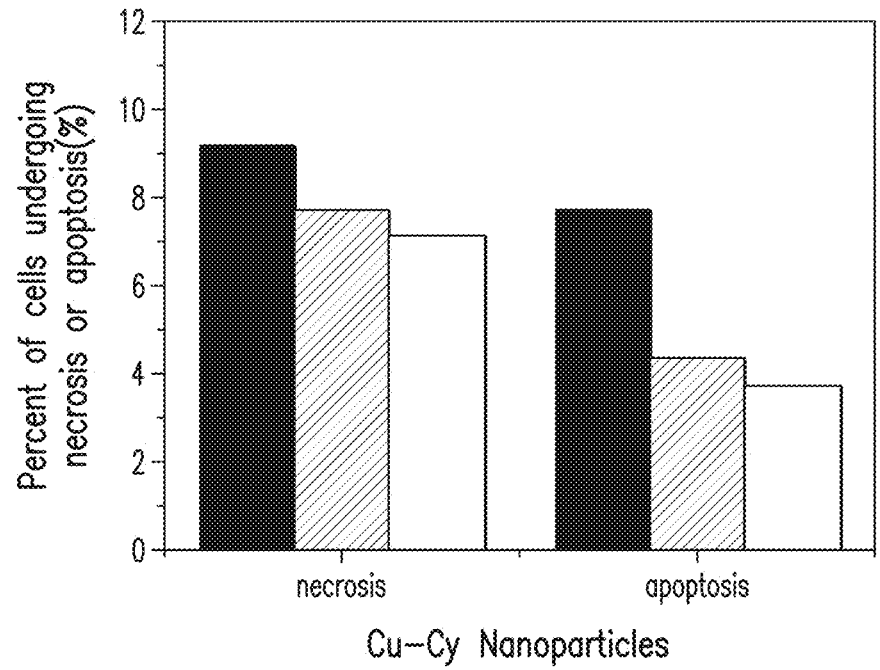
FIGS. 12A and 12B graphically depict the percentage of cells undergoing necrosis and apoptosis.
Figure 12B:
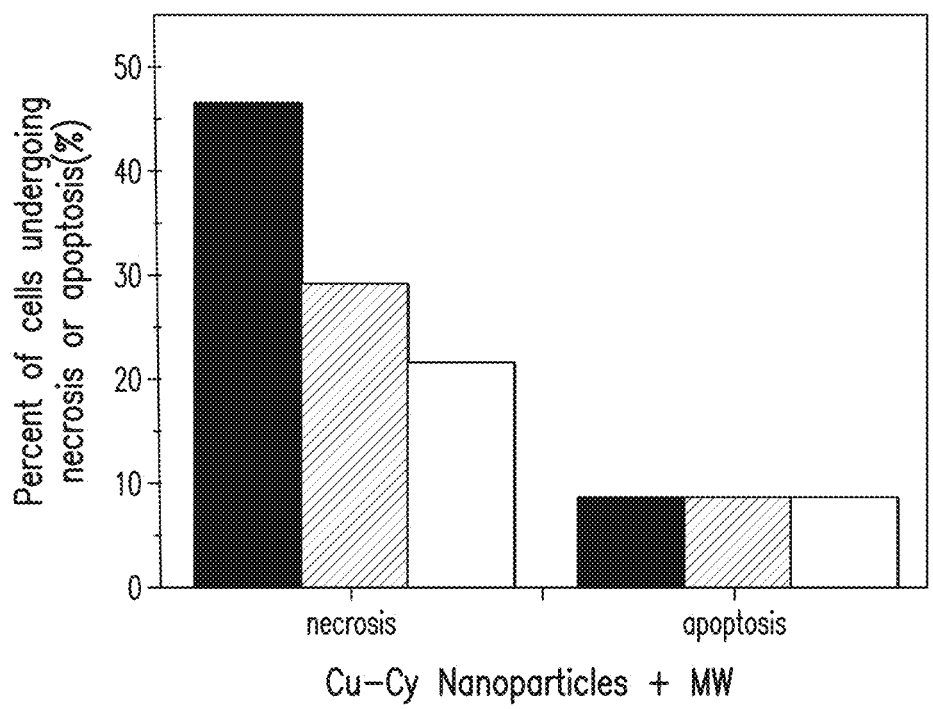

FIG. 10A is the fluorescent visualization of tumor cells treated with 25 mg/mL Cu-Cy and irradiated with microwave radiation. FIG. 10B is the visualization of tumor cells treated with 6.25 mg/mL Cu-Cy and irradiated with microwave radiation. FIG. 10C is visualization of tumor cells treated with saline and irradiated with microwave radiation. FIG. 10D is visualization of tumor cells treated with 25 mg/mL Cu-Cy and irradiated with ultra violet radiation. FIG. 10E is visualization of tumor cells treated with 6.25 mg/mL Cu-Cy and irradiated with ultra violet radiation. FIG. 10F is visualization of tumor cells treated with saline and irradiated with ultraviolet radiation. FIG. 10G is visualization of tumor cells treated with 25 mg/mL Cu-Cy without radiation. FIG. 10H is visualization of tumor cells treated with 6.25 mg/mL Cu-Cy without radiation. FIG. 10I is visualization of tumor cells treated with saline without radiation. FIG. 10A and FIG. 10D indicate the that the concentration of 25 mg/mL of Cu-Cy provides for greater visualization of the nanoparticles.

3. Quantitative Detection of Intracellular Singlet Oxygen

The quantitative detection of intracellular singlet oxygen was conducted by means of the oxidation-sensitive fluorescent probe (DCFH-DA). The cells in culture plates were co-cultured with different concentrations (0, 6.25, and 25 μg/mL) of Cu-Cy nanoparticles for 24 hours, washed three times with PBS, and incubated in a 400 μL DCFH-DA solution at 37° C. for 30 minutes. The cells were washed gently for three times with DMEM and 400 μL of DMEM was added to each plate. The cells in plate A were exposed to MW at 20 W for 5 minutes. The cells in plate B were used for comparison without any treatments. Fluorescence measurement was performed on a Guava Easy Cyte 5HT flow cytometer (Millipore, USA) using 488 nm excitation and a 525 nm filter for DCF detection. For each sample, 6,000 cells were collected for the measurement.

Figure 23A:
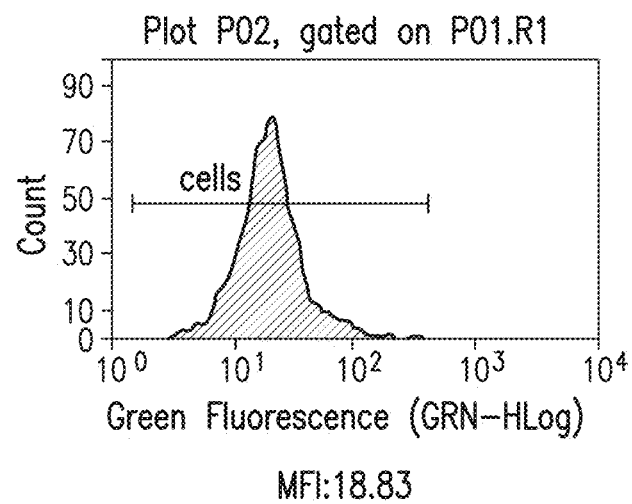
FIGS. 23A-23F depict the quantitative detection of intracellular singlet oxygen as measured by the oxidation-sensitive probe (DCFH-DA) using flow cytometry. The mean fluorescence intensity (MFI) is an indication of the singlet oxygen concentration and thus the oxidative stress in the UMR-106 cells.
Figure 23B:
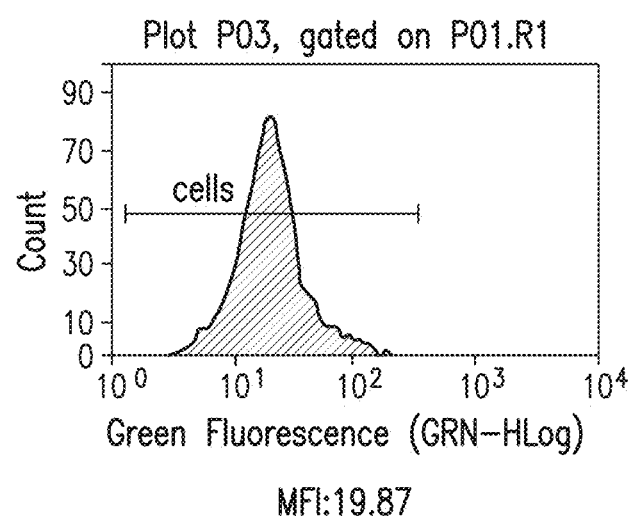
Figure 23C:
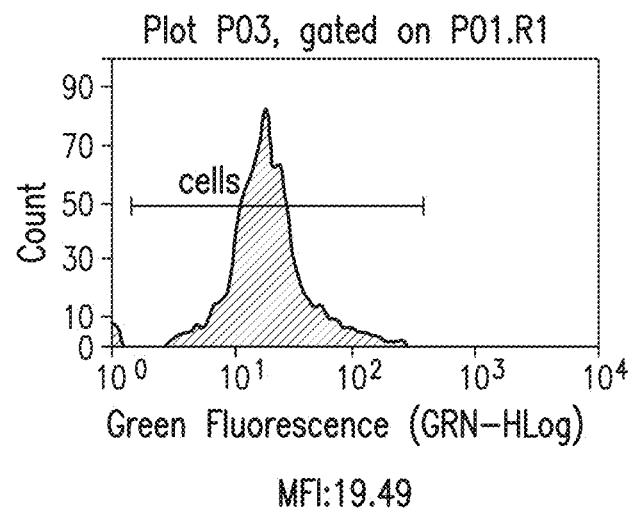
Figure 23D:
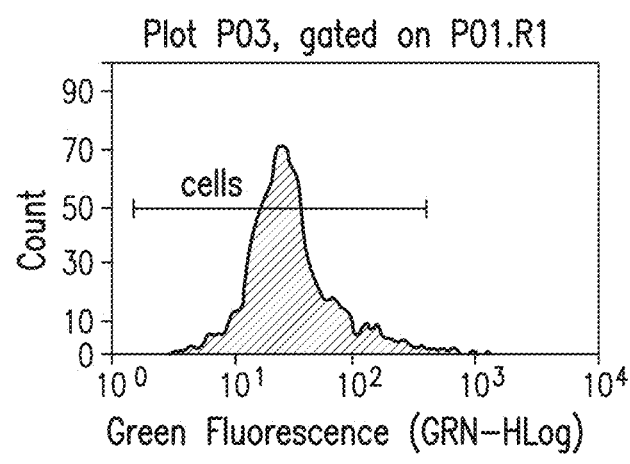
Figure 23E:
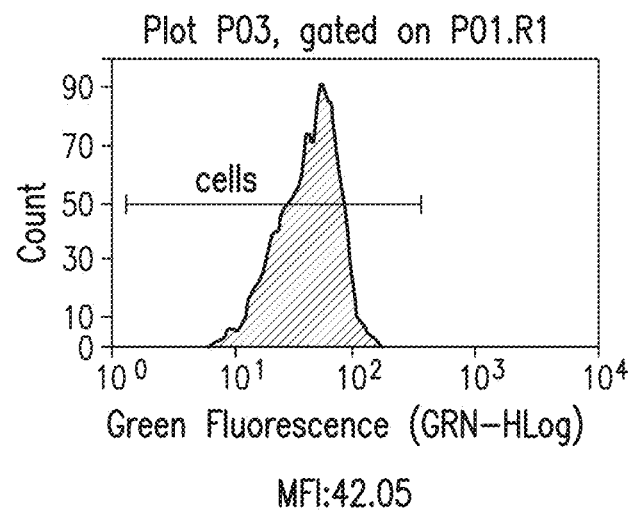
Figure 23F:
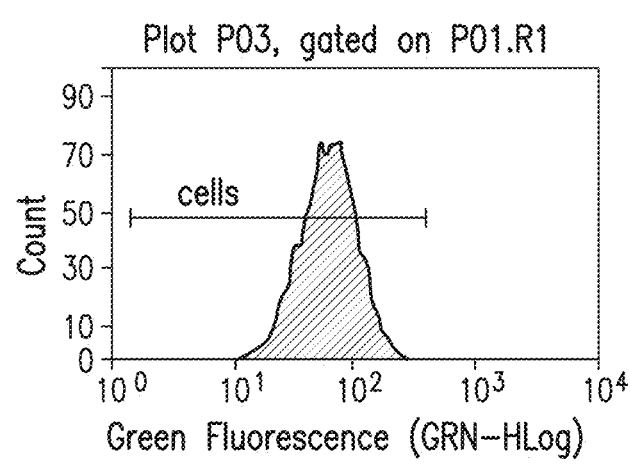

FIG. 23A is the spectrum obtained from the control sample that contains no Cu-Cy nanoparticles. FIG. 23B and FIG. 23C are cells treated with 6.25 and 25 µg/mL Cu-Cy respectively. FIG. 23D is the spectrum of cells irradiated at 20 W for 5 minutes. FIG. 23E depicts cells treated with 6.25 µg/mL Cu-Cy and MW at 20 W for 5 minutes. FIG. 23F depicts cells treated with 25 µg/mL Cu-Cy and MW at 20 W for 5 minutes The quantitative detection of intracellular fluorescence intensity was conducted using flow cytometry (FIG. 23). The mean fluorescence intensity (MFI) reflects the intracellular oxidative stress in the UMR-106 cells. These results indicate that the MFI is always higher in the UMR-106 cells treated with microwave radiation (FIGS. 23D-23F) than in the cells treated without microwave radiation (FIGS. 23A-23C). The MFI increases with increasing Cu-Cy concentration. The MFI for the cells treated with microwave radiation and 25 µg/ml Cu-Cy (FIG. 23F) is two times higher comparing to the cells with MW alone (FIG. 23D) and is three times higher than the control (FIG. 23A). Comparing extended data FIGS. 1A and D, it can be seen that the level of intracellular singlet oxygen is also slightly increased in the UMR-106 cells stimulated by low doses of microwave (20 W for 5 min). The results are summarized in the supplementary TABLE I herein below.

TABLE I

| Cu—Cy conc. µg/mL | Sample irradiated | DCF intensity (MFI) |
|---|---|---|
| 0.0 | No | 18.83 ± 2.15 |
| 6.25 | No | 19.87 ± 1.78 |
| 25 | No | 19.49 ± 1.83 |
| 0.0 | Yes | 26.40 ± 3.31 |
| 6.25 | Yes | 42.05 ± 4.44 |
| 25 | Yes | 42.05 ± 4.44 |

These observations show that the combination of Cu-Cy nanoparticles and microwave can effectively produce singlet oxygen for cancer destruction.

Apoptosis and necrosis are the two processes for cell death that can be analyzed by flow cytometry as shown in FIG. 11. FIGS. 11A-F depict the apoptosis and necrosis of UMR-106 cell as analyzed by Flow Cytometry. FIG. 11A represents cells treated with 25 µg/mL Cu-Cy. FIG. 11B represents cells treated with 6.25m/mL Cu-Cy. FIG. 11C are control cells. FIG. 11D represents cells treated with 25 µg/mL Cu-Cy and MW at 20 W for 5 minutes. FIG. 11E represents cells treated with 6.25m/mL Cu-Cy and MW at 20 W for 5 minutes. FIG. 11F are control cells that were treated with MW at 20 W for 5 minutes.

As can be seen from FIGS. 10A-10F, no obvious difference is observed in terms of the number of cells undergoing apoptosis or necrosis ($p_{apoptosis}$<0.01, $p_{necrosis}$<0.05 for 6.25m/mL) or ($p_{apoptosis}$<0.01, $p_{necrosis}$<0.01 for 0 µg/mL). However, for the UMR-106 cells treated with 25 µg/mL Cu-Cy nanoparticles for 24 hours, the total cell numbers for apoptosis or necrosis increased, while there was no significant difference between the apoptosis and necrosis. Comparing the treatment with Cu-Cy nanoparticles with and without microwave radiation, the apoptosis in each treatment increased from 4% (without microwave radiation) to 8% with Microwave radiation. There is almost no difference between the treatments with the concentrations of Cu-Cy at 0 µg/mL, 6.25 µg/mL and 25 µg/mL. For necrosis, the cell death is increased largely in the microwave treatment. The necrosis cell death for the treatment at 25 µg/mL activated with microwave radiation approaches almost 50%, and for the treatment at each concentration, the microwave radiation induced necrosis cell death is much higher than the apoptosis cell death. All these indicate that the combination of Cu-Cy nanoparticle photosensitizers and microwave radiation is an effective method for cancer treatment.

In Vitro Cell Studies of Microwave Induced Photodynamic Therapy

Figure 20:
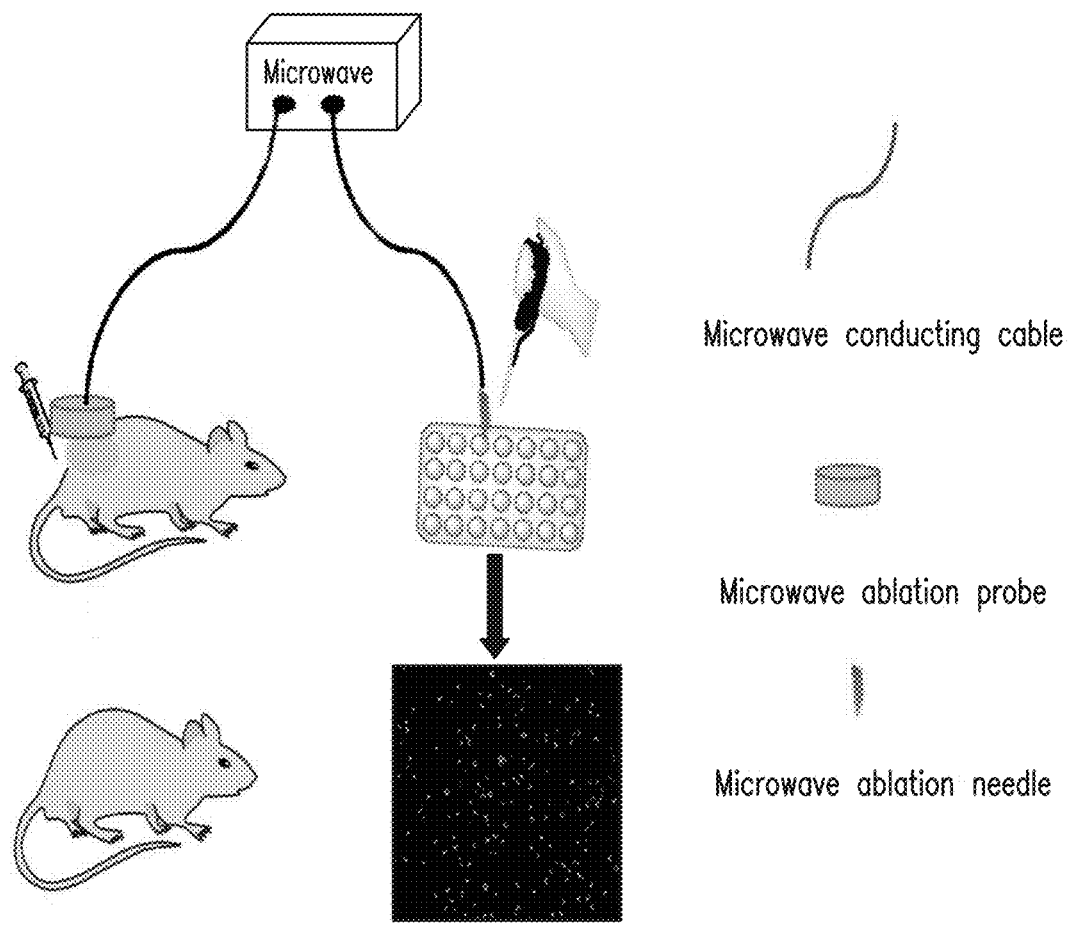
FIG. 20 is a pictorial representation of the procedures described herein for testing the effectiveness of the disclosed methods for treating cancer.

The UMR-106 cells were seeded into a 6-well plate at a density of $2 \times 10^4$ cells/mL and incubated at 37° C. in a humidified atmosphere of 5% v/v $CO_2$ for 24 h. Then, different concentrations (0, 6.25, and 25 µg/mL) of Cu-Cy nanoparticles solution were added to the plate at 400 µL per well and the microwave is delivered to the cells through a radiator probe, as schematically shown in FIG. 20. The cell viability was determined by the live/dead staining after incubation with Cu-Cy nanoparticles for 24 h by MW at 20 W for either 5 or 10 minutes. The cells were rinsed gently with PBS, and then 100 µL solutions of calcein AM and ethidium homodimer (Sigma, USA) were added. The cells were stained at 37° C. for 30 min and then visualized with a fluorescence microscope (Olympus BX51, Olympus Corporation, Japan).

FIGS. 2A-2C are control cells without adding Cu-Cy nanoparticles. FIG. 2A depicts cells that were not irradiated. FIG. 2B depicts cells that were irradiated at 20 W for 5 minutes. FIG. 2C depicts cells that were irradiated at 20 W for 10 minutes. FIGS. 2D and 2E depict cells treated with 6.25 µg/mL of Cu-Cy nanoparticles. The cells in FIG. 2D were not irradiated. The cells in FIG. 2E were irradiated at 20 W for 5 minutes. FIG. 2F represents cells treated with 25 µg/mL of Cu-Cy nanoparticles and MW at 20 W for 10 minutes. FIG. 2G represents cells treated with 25 µg/mL of Cu-Cy nanoparticles without irradiation. FIG. 2H represents cells treated with 25 µg/mL of Cu-Cy nanoparticles and MW at 20 W for 5 minutes. FIG. 2I represents cells treated with 25 µg/mL of Cu-Cy nanoparticles and MW at 20 W for 10 minutes.

As seen in FIG. 2D and FIG. 2G only a few cells were dead (red) when treated with Cu-Cy nanoparticles. However, with microwave irradiation at 20 W for 5 min, some UMR-106 cells were vague and dead as seen in FIGS. 2E, 2F, 2H and 2I. Cells treated with 6.25 µg/mL Cu-Cy nanoparticles show more cell death using longer irradiation times. All the cells are almost dead by treating with 25 µg/mL of Cu-Cy nanoparticles and MW at 20 W for 10 minutes.

Figure 2:
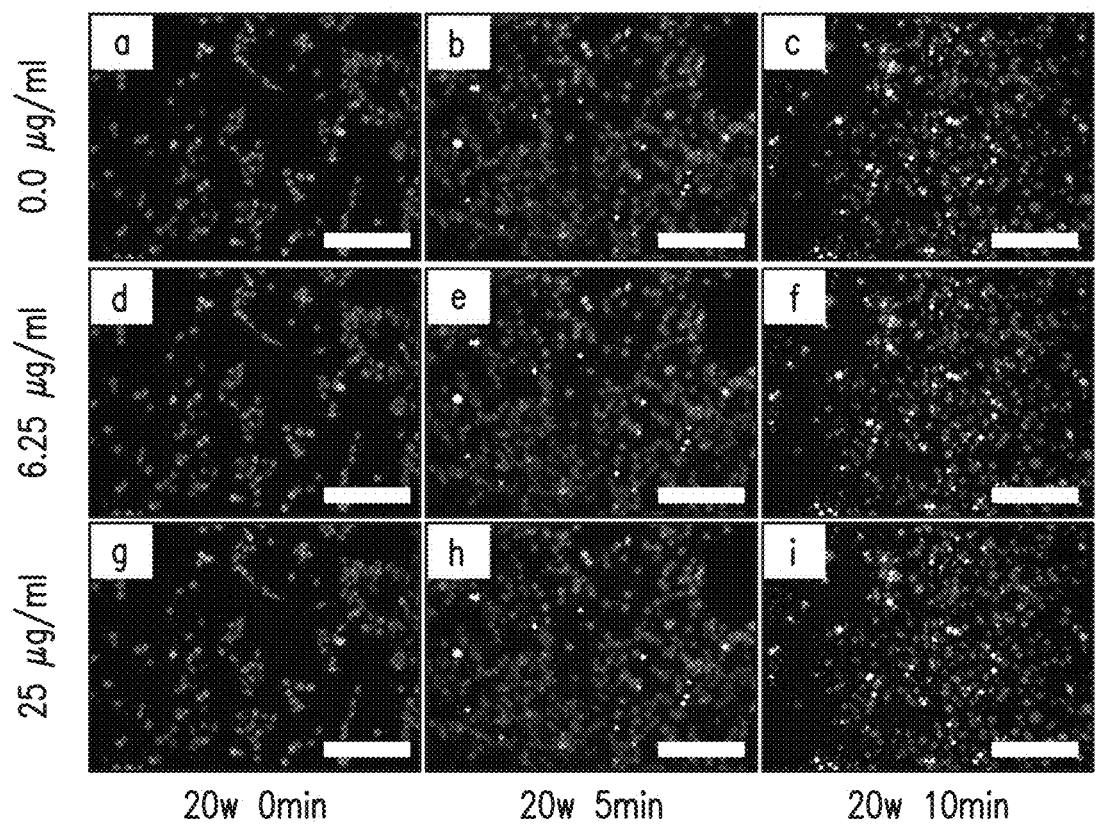
FIGS. 2A-2I are the fluorescent visualization of live/dead staining images of UMR-106 cancer cells.
Figure 3:
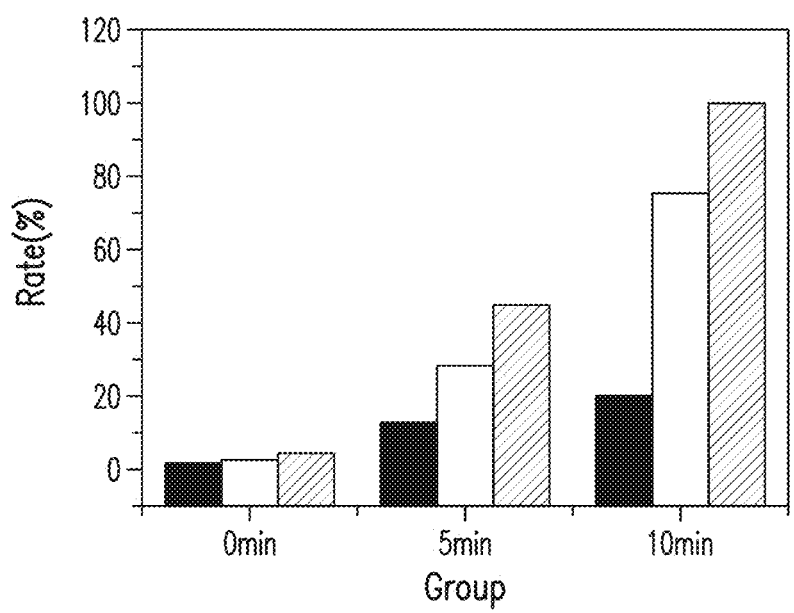
FIG. 3 depicts the rate of cell death for cells treated with various concentrations of Cu-Cy nanoparticles over time. The black bars represent the control group, white bars are 6.25 μg/mL of Cu-Cy nanoparticles and the hatched bars represent a concentration of 25 μg/mL.

The results depicted in FIGS. 2A-2I are quantified and shown in FIG. 3. It is seen that the rate of cell death increases with the concentration of Cu-Cy nanoparticles and MW irradiation time. The black bars represent the control group, red bars are 6.25 µg/mL of Cu-Cy nanoparticles and the blue bars represent a Cu-Cy concentration of 25 µg/mL.

In Vivo Animal Studies of Microwave Induced Photodynamic Therapy

To create the UMR-106 tumor xenografts, we used six- to eight-week-old female nude mice (C57BL/6, Medical Experimental Animal Center of Guangdong Province, China). A suspension of $1 \times 10^6$ UMR-106 cells was injected subcutaneously into both the shoulder and the leg of nude mice. For microwave treatment, the microwave is delivered directly to the tumors through a radiator probe, as schematically shown in FIG. 20. The animals were monitored daily for tumors growth. When the tumors reached about 5-8 mm in diameter, the mice were anesthetized with 1% chloral hydrate solution and randomly divided into three groups: Cu-Cy, irradiation alone and Cu-Cy followed by irradiation (n=6 for each group). In the Cu-Cy and Cu-Cy plus irradiation groups, normal saline and 30, 50 and 100 μL of Cu-Cy nanoparticles (concentration: 1 mg/mL) were injected intratumorally in the anesthetized mice. In the microwave irradiated group, 30, 50, or 100 μL of normal saline was injected, respectively. After 30 min post-injection, the tumors on the mice in the irradiation alone and Cu-Cy plus irradiation groups were irradiated with microwave radiation at 20 W for 5 min. Tumor size was measured using a digital caliper every day after the radiation treatment started. Tumor volume was calculated using the following formula: π/6× larger diameter×(smaller diameter). A tumor growth curve was derived from the animals assigned to day 14 in each group. The animals were euthanized on day 14. The tumors were surgically dissected, and tumor volumes (in cubic millimeters) were measured. The tumors were preserved in 4% paraformaldehyde solution, and then were dehydrated and embedded in paraffin following routine methods. Finally, the frozen specimens were cut into cryosections, and two adjacent 5 μm thick cryosections were used for Ki-67 (ab15580, Abcam, England) immunohistochemistry (IHC) and immunofluorescent (IF) staining to assess tumor proliferation. One of the adjacent 5 μm thick sections was used for hematoxylin and eosin (H&E) staining to observe the morphological changes in the cells and tissues. Images of the tumor sections stained by the anti-Ki-67 antibody and H&E were visualized with a fluorescence microscope (Olympus BX51, Japan).

Figure 4:
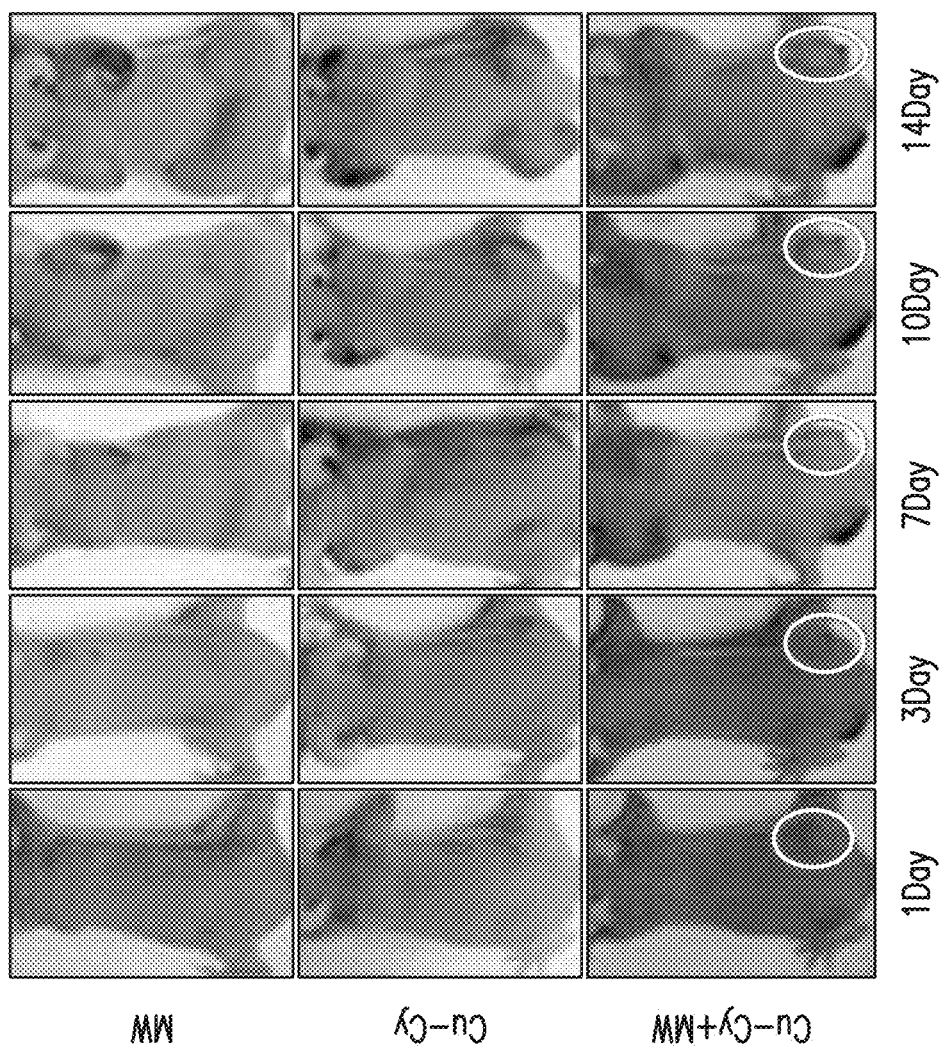
FIG. 4 is a series of photographs of 6-8 week old female nude mice (C57BL/6) that were treated with a suspension of $1 \times 10^6$ UMR-106 cancer cells that was injected into the shoulders and legs of each mouse. Animals were selected for treatment once the tumors size was from 5-8 mm in diameter. After treatment the animals were evaluated at days 1, 3, 7, 10 and 14 as indicated in FIG. 4. The animal shown in the top row represents the controls that were all injected with normal saline as follows: left shoulder 100 μL, right shoulder 20 μL, left leg 50 μL and right leg 100 μL. These animals were then subjected to microwave irradiation at 20 W for 5 minutes then sacrificed on day 14. The animals pictured in the second and third rows represent the groups that were injected with a solution containing 1 mg/mL of Cu-Cy nanoparticles as follows: left shoulder 100 μL, right shoulder 20 μL, left leg 50 μL and right leg 100 μL. The animal in the second row represents the group that were not irradiated. The animal in the third row represents animals that were treated with 20 W of radiation for 5 minutes directly on the tumors.

FIG. 4 shows the day to day tumor growth of a representative animal in each protocol. The animals were evaluated at days 1, 3, 7, 10 and 14. The animal shown in the top row represents the controls that were all injected with normal saline as follows: left shoulder 10 μL, right shoulder 20 μL, left leg 50 μL and right leg 100 μL. These animals were then subjected to microwave irradiation at 20 W for 5 minutes and sacrificed on day 14. The animals in the second and third rows represent the groups that were injected with a solution containing 1 mg/mL of Cu-Cy as follows: left shoulder 10 μL, right shoulder 20 μL, left leg 50 μL and right leg 100 μL. The animals in the second row were not irradiated but the animals in the third row were treated with 20 W MW for 5 minutes directly on the tumors.

The animals were euthanized and decapitated on the fourteenth day. The tumors were surgically dissected and shown in FIG. 5. It is seen that the tumors treated with normal saline or Cu-Cy only (top and middle rows) grew to larger volumes than those treated with Cu-Cy and MW irradiation. The similar size of the tumors treated with 20, 50 or 100 μl of Cu-Cy nanoparticles confirms that these Cu-Cy nanoparticles alone have little effect on the tumor growth. However, when the nanoparticles are activated by microwave radiation, Cu-Cy nanoparticles (at 50 μL and 100 μL) can greatly shrink the tumor volume (bottom row of FIG. 5). These observations are consistent with the results shown in the top left of FIG. 5. The preliminary results show that Cu-Cy nannoparticles can be activated by microwave radiation to produce singlet oxygen for tumor destruction.

As depicted in FIG. 4, the tumors treated with Cu-Cy alone were smaller than the tumors treated with normal saline (control), particularly for the tumor in the right leg of the Cu-Cy group (Cu-Cy dosages of 100 μL). There is, however, no statistically significant difference between the microwave control group and group receiving only Cu-Cy without irradiation. This suggests that the Cu-Cy nanoparticles exhibit a slight toxicity in vivo; however, Cu-Cy particles alone do not significantly reduce the tumor size or suppress their growth. With microwave irradiation (bottom row), the tumor growth was greatly reduced at the dosages of 50 μL and 100 μL Cu-Cy.

Figure 5:
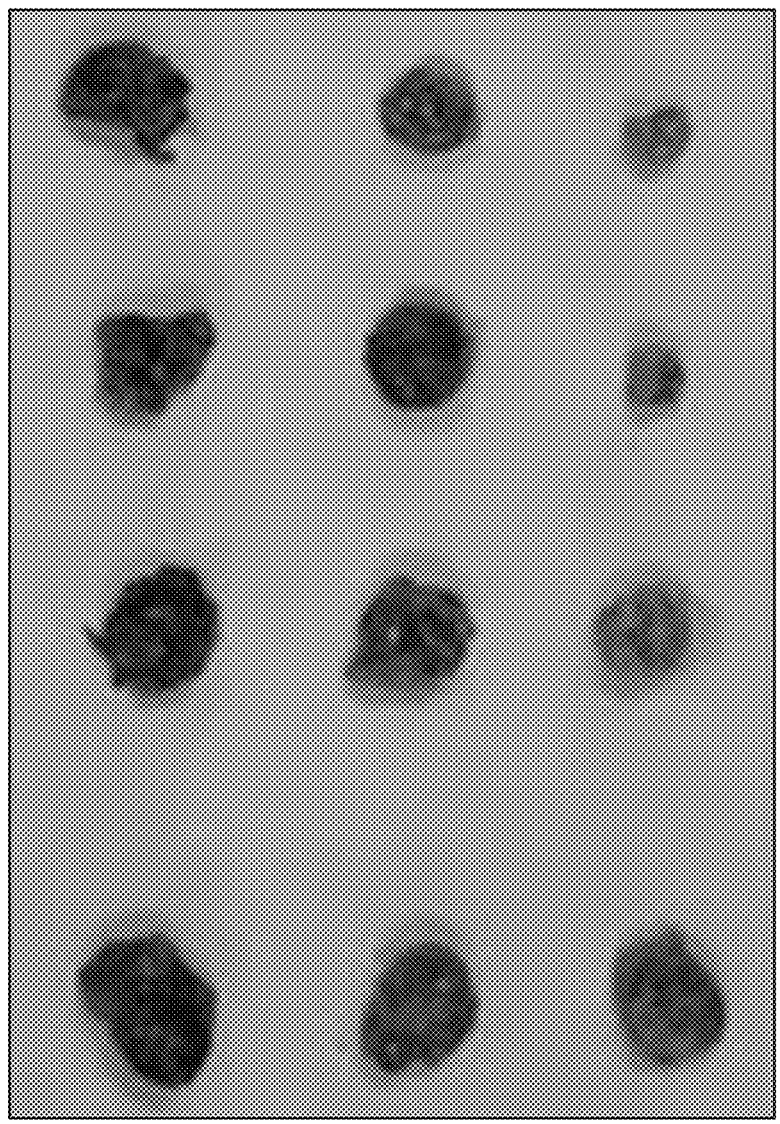
FIG. 5 depicts the tumors excised from the animals of FIG. 4 that were sacrificed on day 14. Reading left to right, each row depicts tumors from the right shoulder (RS), left shoulder (LS), right leg (RL) and left leg (LL).

FIG. 5 depicts the tumors excised from the animals of FIG. 4 that were sacrificed on day 14. Reading left to right, each row depicts tumors from the right shoulder (RS), left shoulder (LS), right leg (RL) and left leg (LL).

FIG. 6 depicts the tumor growth curves for the various animal groups. FIG. 6A represents growth of tumors in the left shoulder (thin line), right shoulder (heavy dashed line), left leg (thin dashed line) and right leg (thick line) of the animal from row 1 of FIG. 4 sacrificed on day 14. This animal received saline injections and microwave treatment. FIG. 6B represents the growth of tumors in the left shoulder (thin line), right shoulder (heavy dashed line), left leg (thin dashed line) and right leg (thick line) of the animal from row 2 of FIG. 4 sacrificed on day 14. This animal received injections of Cu-Cy but did not receive microwave treatment. FIG. 6C represents the growth of tumors in the left shoulder (thin line), right shoulder (heavy dashed line), left leg (thin dashed line) and right leg (thick line) of the animal from row 3 of FIG. 4 sacrificed on day 14. This animal received injections of Cu-Cy and direct radiation of the tumors with 20 W microwave irradiation for 5 minutes.

Figure 6A:
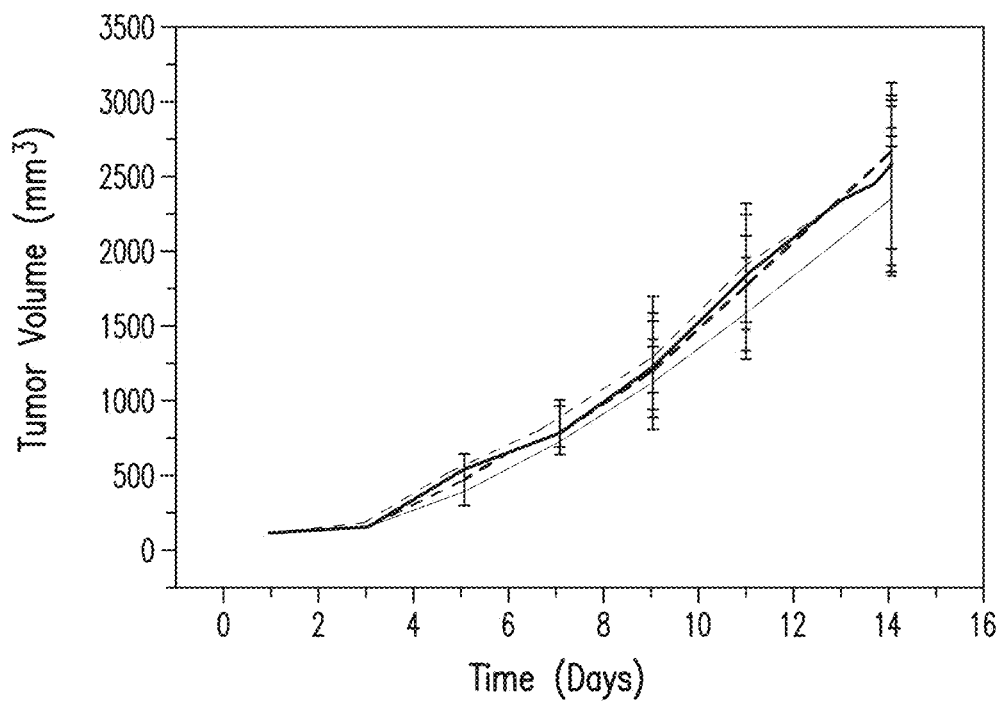
FIG. 6A represents growth of tumors in the left shoulder (thin line), right shoulder (heavy dashed line), left leg (thin dashed line) and right leg (thick line) of the animal from row 1 of FIG. 4 sacrificed on day 14. This animal received saline injections and microwave treatment.
Figure 6B:
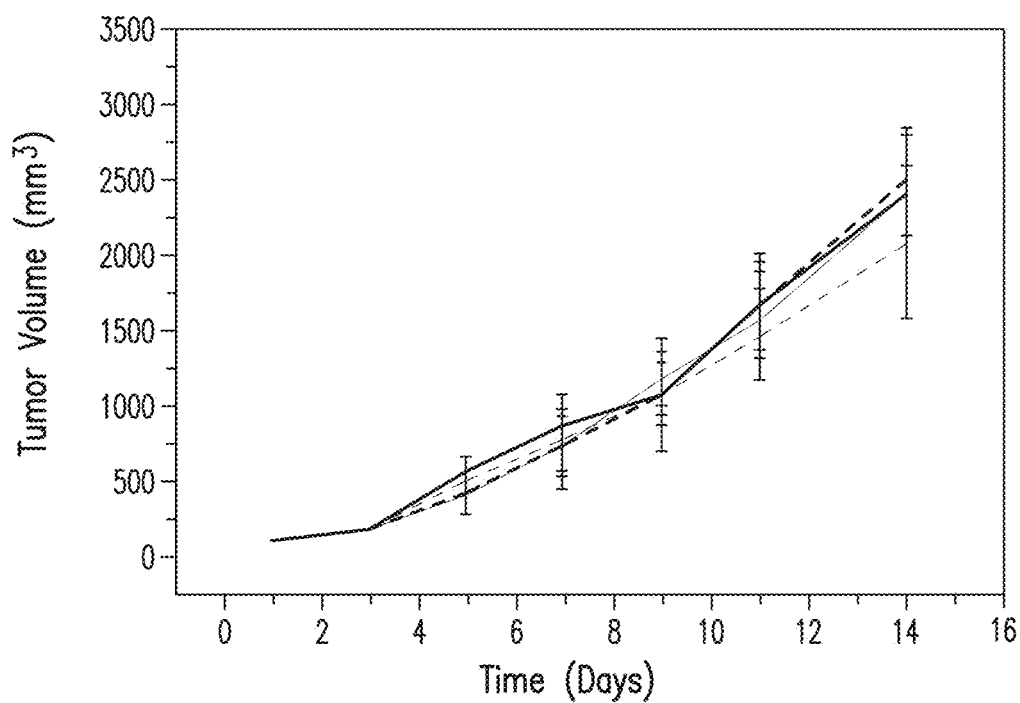
FIG. 6B represents the growth of tumors in the left shoulder (thin line), right shoulder (heavy dashed line), left leg (thin dashed line) and right leg (thick line) of the animal from row 2 of FIG. 4 sacrificed on day 14. This animal received injections of Cu-Cy but did not receive microwave treatment.
Figure 6C:
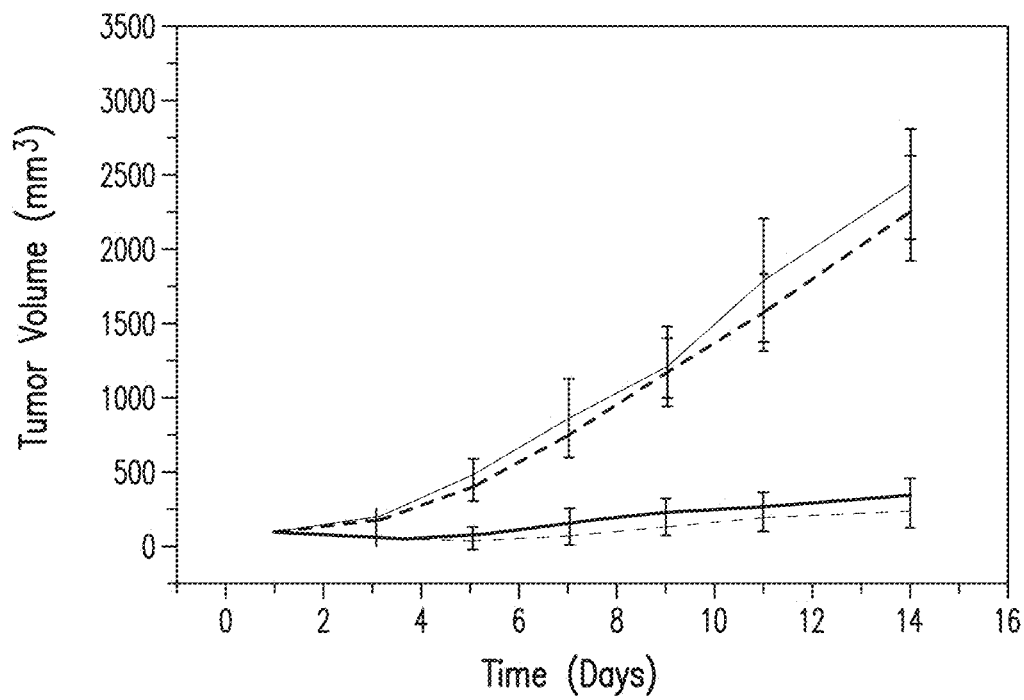
FIG. 6C represents the growth of tumors in the left shoulder (thin line), right shoulder (heavy dashed line), left leg (thin dashed line) and right leg (thick line) of the animal from row 3 of FIG. 4 sacrificed on day 14. This animal received injections of Cu-Cy and direct radiation of the tumors with 20 W microwave irradiation for 5 minutes.
Figure 6D:
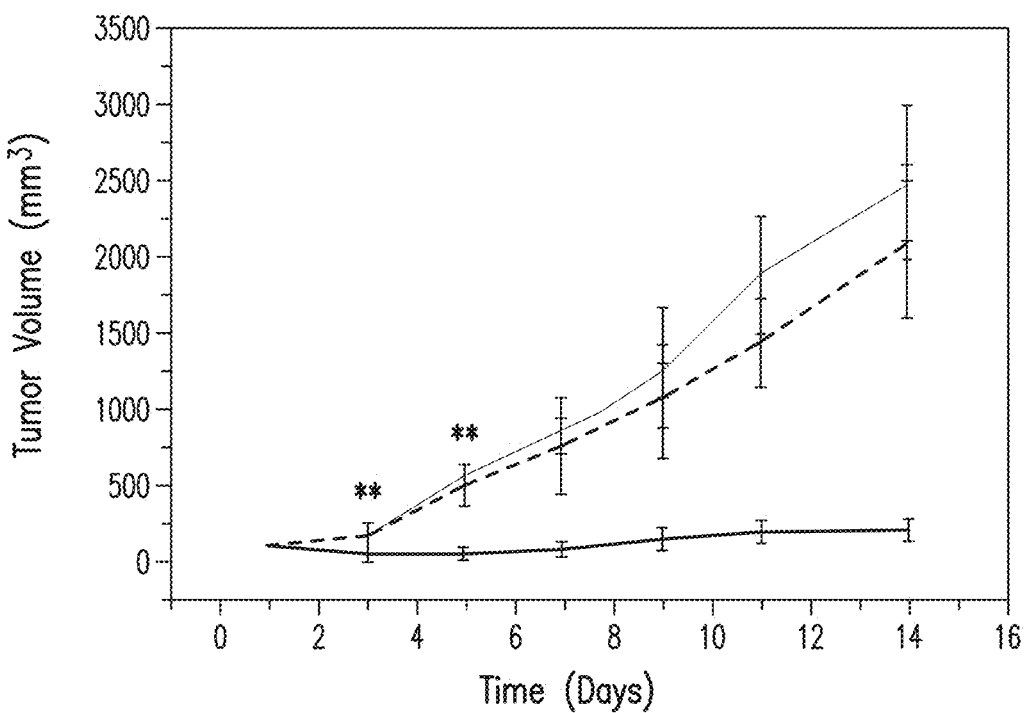
FIG. 6D compares the tumor growth for the right leg tumors of the three animals sacrificed on day 14; 100 μL saline injection followed by 20 W irradiation for 5 minutes (thin solid line), 100 μL of 1 mg/mL Cu-Cy with no irradiation (dashed line), and 100 μL of 1 mg/mL Cu-Cy followed by 20 W radiation for 5 minutes (solid line). As depicted in FIG. 6D, treatment of a tumor with Cu-Cy followed by irradiation led to no significant tumor growth even after 14 days.

FIG. 6D compares the tumor growth for the right leg tumors of the three animals sacrificed on day 14; 100 μL saline injection followed by 20 W irradiation for 5 minutes (thin solid line), 100 μL of 1 mg/mL Cu-Cy with no irradiation (dashed line), and 100 μL of 1 mg/mL Cu-Cy followed by 20 W radiation for 5 minutes (solid line). As depicted in FIG. 6D, treatment of a tumor with Cu-Cy followed by irradiation led to no significant tumor growth even after 14 days.

The tumors on different parts of the mice in the microwave and Cu-Cy only groups were similar in size, and no statistically significant difference was observed among them (See FIG. 4 Bottom A and B). In the animals receiving Cu-Cy nanoparticles followed by irradiation, as Cu-Cy dosages increased, the tumor volume decreased (FIG. 6C). A significant difference in tumor volume was observed on day 3 for left leg (LL) versus left shoulder (LS) ($^\#$ $P<0.05$, $^{\#\#}$ $P<0.01$) and right leg (RL) versus left shoulder (LS) (*$P<0.05$, $P<0.01$). A significant difference in tumor volume on the right leg was observed on the day 3 for the animals receiving Cu-Cy nanoparticles and microwave irradiation versus the Cu-Cy nanoparticle only group ($^{\#\#}$ $P<0.01$). This was also true for the animals receiving Cu-Cy nanoparticles and those receiving only microwave irradiation versus ($P<0.01$). No statistically significant difference was observed between the groups receiving only microwave radiation and only Cu-Cy nanoparticles. MW and Cu-Cy groups (FIG. 4D).

A significant number of Cu-Cy nanoparticles were taken up by UMR-106 cells at the concentration of 100 μg/mL. Without wishing to be limited by theory, to investigate the mechanism for the tumor destruction, the production of intracellular singlet oxygen was measured by the DCFH-DA method. The cells were visualized with a fluorescence microscope (FIG. 10) after incubation with Cu-Cy nanoparticle concentrations of 25 μg/ml, 6.25 μg/ml and 0 μg/ml for 24 hours and exposure to ultra violet and microwave radiation respectively. The UMR-106 cells treated 25 μg/ml Cu-Cy nanoparticles activated with UV or microwave radiation emit green fluorescence (FIGS. 9A and 9D) which indicates the production of singlet oxygen in the cells. Control cells or UMR-106 cells that were treated with 6.25

μg/ml Cu-Cy nanoparticles when activated with UV or microwave radiation, no fluorescence was observed. This indicates that no singlet oxygen was created in these cells.

Observation of Cell Death

1. Staining

The UMR-106 cell suspension (400 μL) was seeded into a 24-well cell culture plate at a density of $5\times10^4$ cells/mL. After 24 h of incubation, different concentrations (0, 6.15, and 25 μg/mL) of Cu-Cy nanoparticle solution were added to the plate at 400 μL per well. Upon incubation with Cu-Cy nanoparticles for 24 h, cells in the plate were radiated by MW at 20 W for 5 min. To visualize the changes in the nuclear morphology, UMR-106 cells were measured using Guava Nexin Reagent (Millipore, USA). Briefly, the UMR-106 cells were washed with PBS gently and centrifuged at 1,000 rpm for 5 min. The cell pellets were re-suspended in 100 μL DMEM supplemented with 1% FBS, and then incubated with 100 μL of Annexin V-PE and 7-AAD labeling solution for 20 min at room temperature. Cells were finally analyzed with a Guava EasyCyte 5HT flow cytometer (Millipore, USA) under 488 nm excitation using a 575 nm band-pass filter for Annexin V-PE detection and under 546 nm excitation using a 647 nm filter for 7-AAD detection. The data were analyzed using Guava Nexin Software v2.2.2. Six thousand cells were analyzed.

Figure 7:
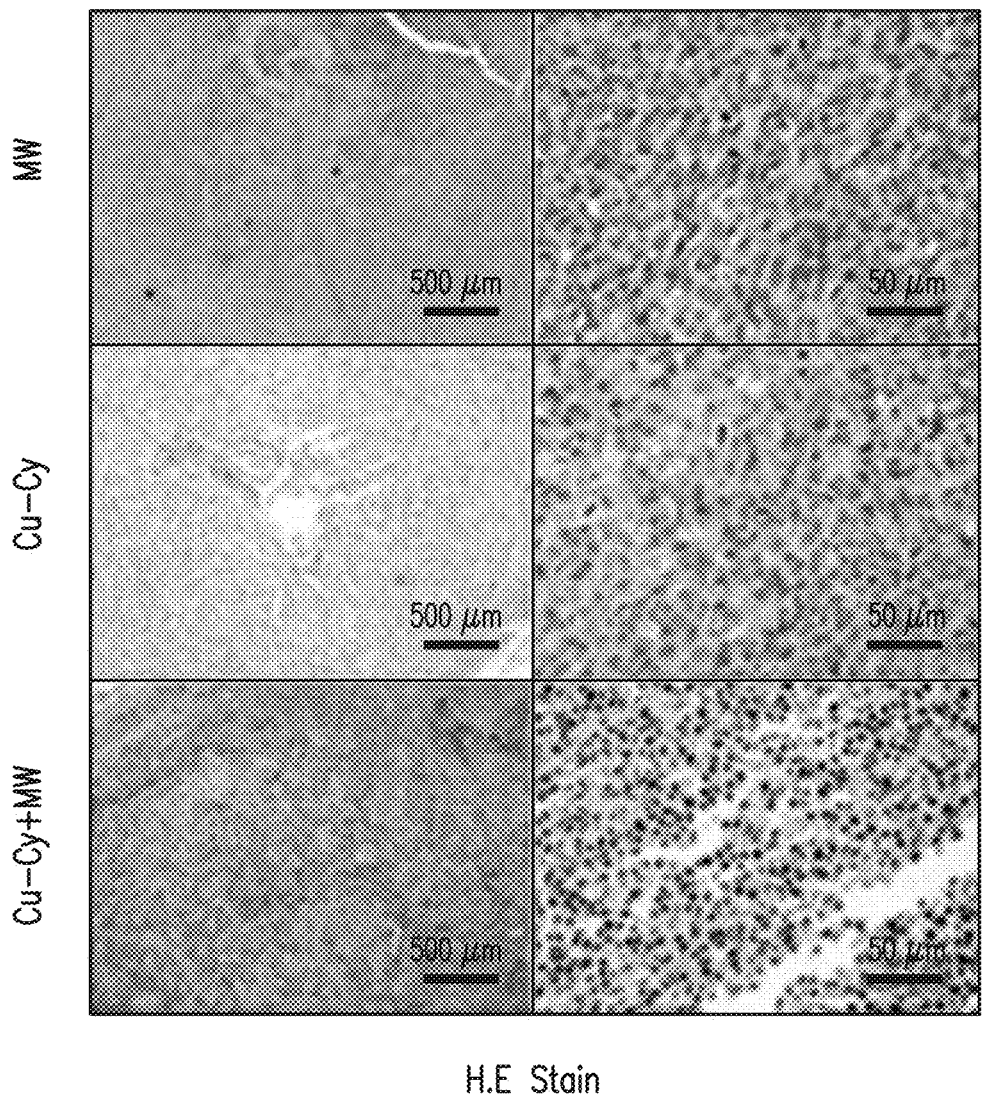
FIG. 7 shows the hematoxylin and eosin (H&E) staining of frozen sections from various tumor samples. Top row are stains of the tumor on the right leg of the animal sacrificed at day 14 depicted in FIG. 4 given 100 μL of saline followed by radiation of 20 W for 5 minutes. Middle row are stains of the tumor from the right leg of the animal sacrificed at day 14 depicted in FIG. 4 given 100 μL of a solution containing 1 mg/mL of Cu-Cy without irradiation. Bottom row are stains of the tumor from the right leg of the animal sacrificed at day 14 depicted in FIG. 4 given 100 μL of a solution containing 1 mg/mL of Cu-Cy followed by radiation of 20 W for 5 minutes.

FIG. 7 shows the hematoxylin and eosin (H&E) staining of frozen sections from various tumor samples. Top row are stains of the tumor from the right leg of the animal sacrificed at day 14 depicted in FIG. 4 given 100 μL of saline followed by radiation of 20 W for 5 minutes. Middle row are stains of the tumor from the right leg of the animal sacrificed at day 14 depicted in FIG. 4 given 100 μL of a solution containing 1 mg/mL of Cu-Cy without irradiation. Bottom row are stains of the tumor from the right leg of the animal sacrificed at day 14 depicted in FIG. 4 given 100 μL of a solution containing 1 mg/mL of Cu-Cy followed by radiation of 20 W for 5 minutes.

The hematoxylin and eosin (H&E) staining (FIG. 7 left) on the tumor tissues shows that the tumor tissues treated only with Cu-Cy nanoparticles or microwave radiation alone, respectively, display no signs of cell damage or injury, and these tumors are composed of malignant cells in a large quantity (FIG. 7 left top and middle rows). In the slide wherein both Cu-Cy and irradiation was empleoyed, the tumor cells show nuclear pyknosis, cytoplasmic edema and some leaking patches of eosinophils, indicating tumor necrosis (FIG. 7 left bottom row).

2. Immuno Staining

For IHC and IF, briefly, after rehydration and antigen retrieval, endogenous peroxidase activity was blocked by incubating with methanol containing 0.3% hydrogen peroxide. Thereafter, sections were incubated overnight with Ki-67 antibody, and then incubated with a secondary Anti-Rabbit IgG (Alexa Fluor 488, Beyotime, China). The slides were counterstained with 4',6-diamidino-2-phenylindole (DAPI)(C1002, Beyotime, China). Images of the tumor sections stained by the anti-Ki-67 antibody were captured under a fluorescence microscope (Olympus BX51, Japan).

Figure 8:
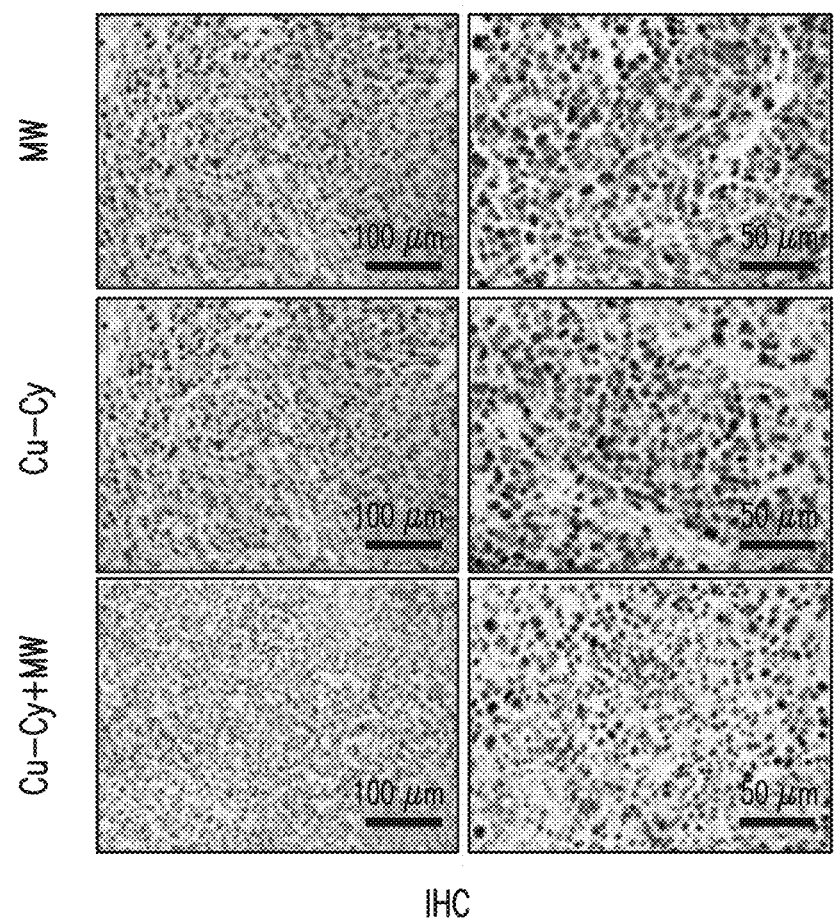
FIG. 8 shows the immunohistochemistry (IHC) and immunofluorescence (IF) staining of frozen sections from various tumor samples with Ki-67 antigen. Top row are stains of the tumor from the right leg of the animal sacrificed at day 14 depicted in FIG. 4 given 100 μL of saline followed by radiation of 20 W for 5 minutes. Middle row are stains of the tumor from the right leg of the animal sacrificed at day 14 depicted in FIG. 4 given 100 μL of a solution containing 1 mg/mL of Cu-Cy without irradiation. Bottom row are stains of the tumor from the right leg of the animal sacrificed at day 14 depicted in FIG. 4 given 100 μL of a solution containing 1 mg/mL of Cu-Cy followed by radiation of 20 W for 5 minutes.

FIG. 8 shows the immunohistochemistry (IHC) and immunofluorescence (IF) staining of frozen sections from various tumor samples with Ki-67 antigen. Top row are stains of the tumor from the right leg of the animal sacrificed at day 14 depicted in FIG. 4 given 100 μL of saline followed by irradiation of 20 W for 5 minutes. Middle row are stains of the tumor from the right leg of the animal sacrificed at day 14 depicted in FIG. 4 given 100 μL of a solution containing 1 mg/mL of Cu-Cy without irradiation. Bottom row are stains of the tumor from the right leg of the animal sacrificed at day 14 depicted in FIG. 4 given 100 μL of a solution containing 1 mg/mL of Cu-Cy followed by irradiation of 20 W for 5 minutes.

Ki-67 is a nuclear non-histone protein that is present at low levels in quiescent cells but is increased in proliferating cells, especially in the G2, M and the latter half of the S phase. Therefore, Ki-67 reactivity, defined as percent tumor cells staining positive as measured by immunohistochemical (IHC) staining, is a specific nuclear marker for cell proliferation. Overexpression is frequently seen in a variety of malignant tissues and associated with worse survival of individuals with cancers. This staining process can measure the percentage of tumor cells that are positive for Ki-67. The more positive cells there are, the more quickly they are dividing and forming new cells. The Ki-67 stain applied to the tumor cells treated with Cu-Cy only, microwave radiation only and Cu-Cy nanoparticles followed by irradiation is shown in FIG. 8 (right). As indicated in FIG. 8 only the combination of treatment with Cu-Cy followed by microwave irradiation was seen to effectively suppress tumor growth.

For the tumors treated with Cu-Cy nanoparticles alone or microwave radiation at 20 W alone, overexpression of Ki67 is observed. Therefore, treatment with Cu-Cy alone or irradiation of tumors with microwave radiation alone does not effectively destroy cancer cells or suppress their proliferation. Most tumor cells were killed when treated with Cu-Cy followed by microwave irradiation. In small amount of live tumor cells, the expression of Ki67 was largely reduced.

Biodistribution

Figure 13A:
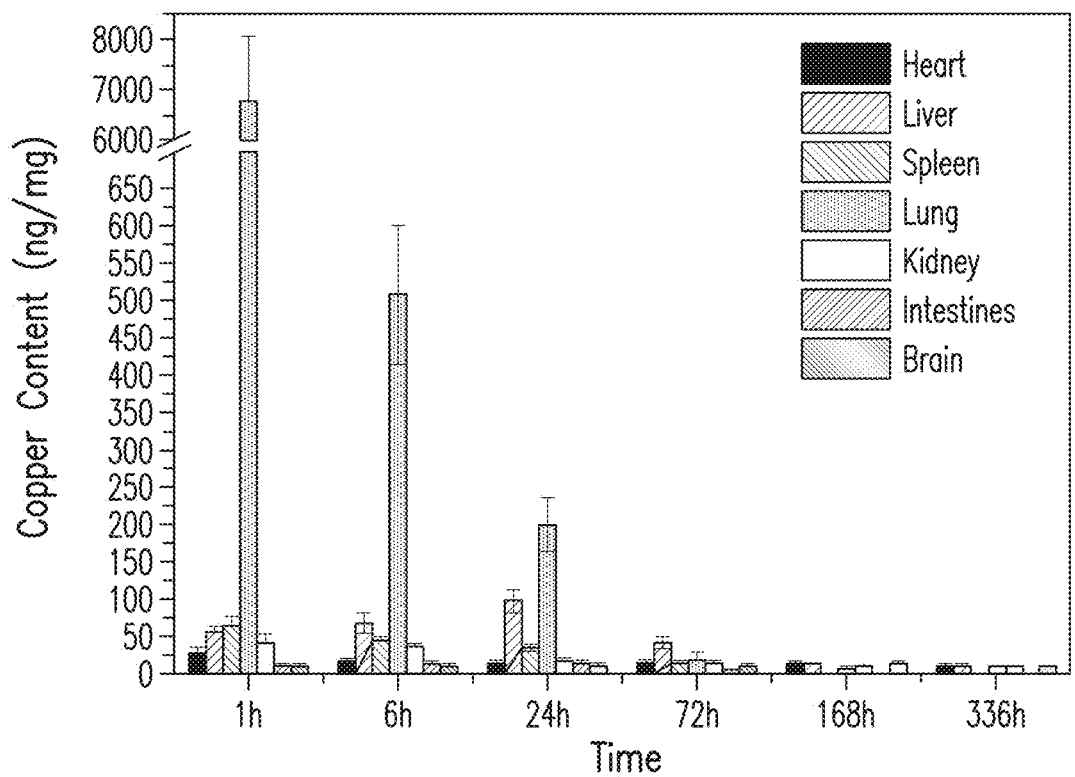
FIGS. 13A-13C, show the biodistribution of Cu-Cy nanoparticles in various main organs, i.e., heart, liver, spleen, lung, kidney, brain, intestines as read from left to right. At 1 hour, as seen in FIG. 13A and FIG. 13B, the copper concentration in the lungs (4$^{th}$ bar from the left) far exceeded the other organs. After 72 hr, the high dose group and low dose group were completely back to the normal levels of the control (FIG. 13C).
Figure 13B:
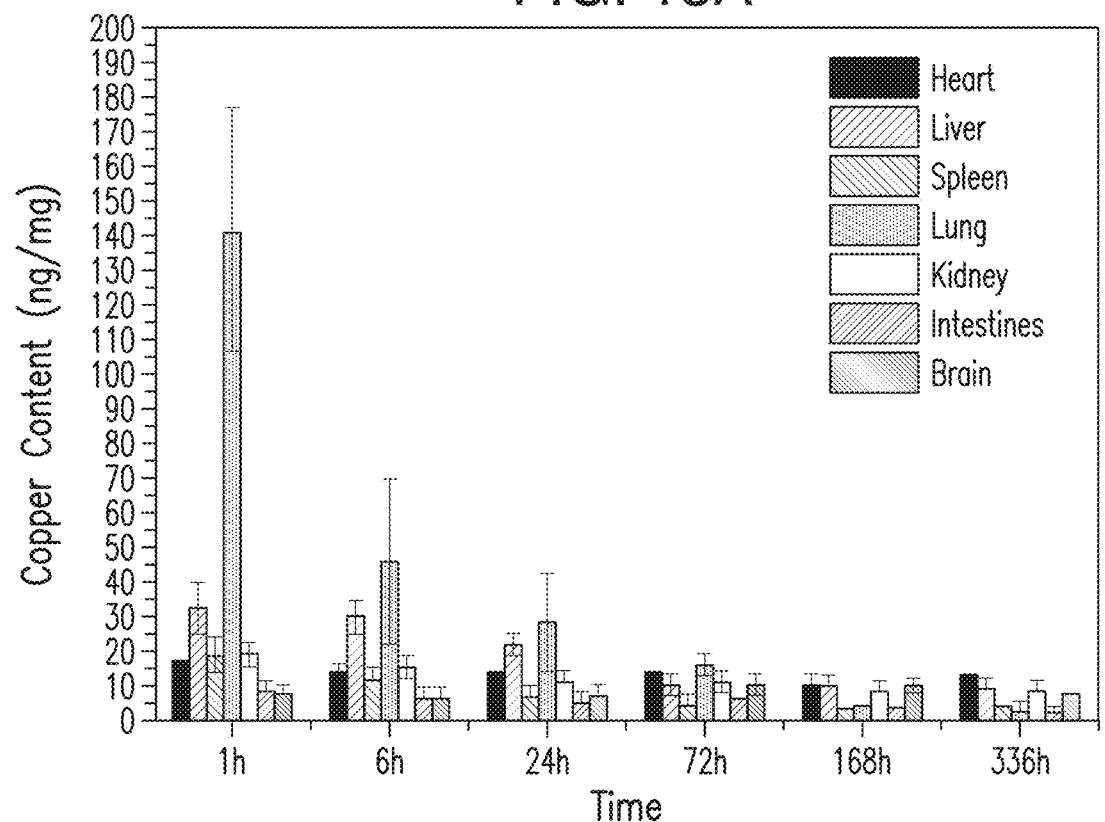
Figure 13C:
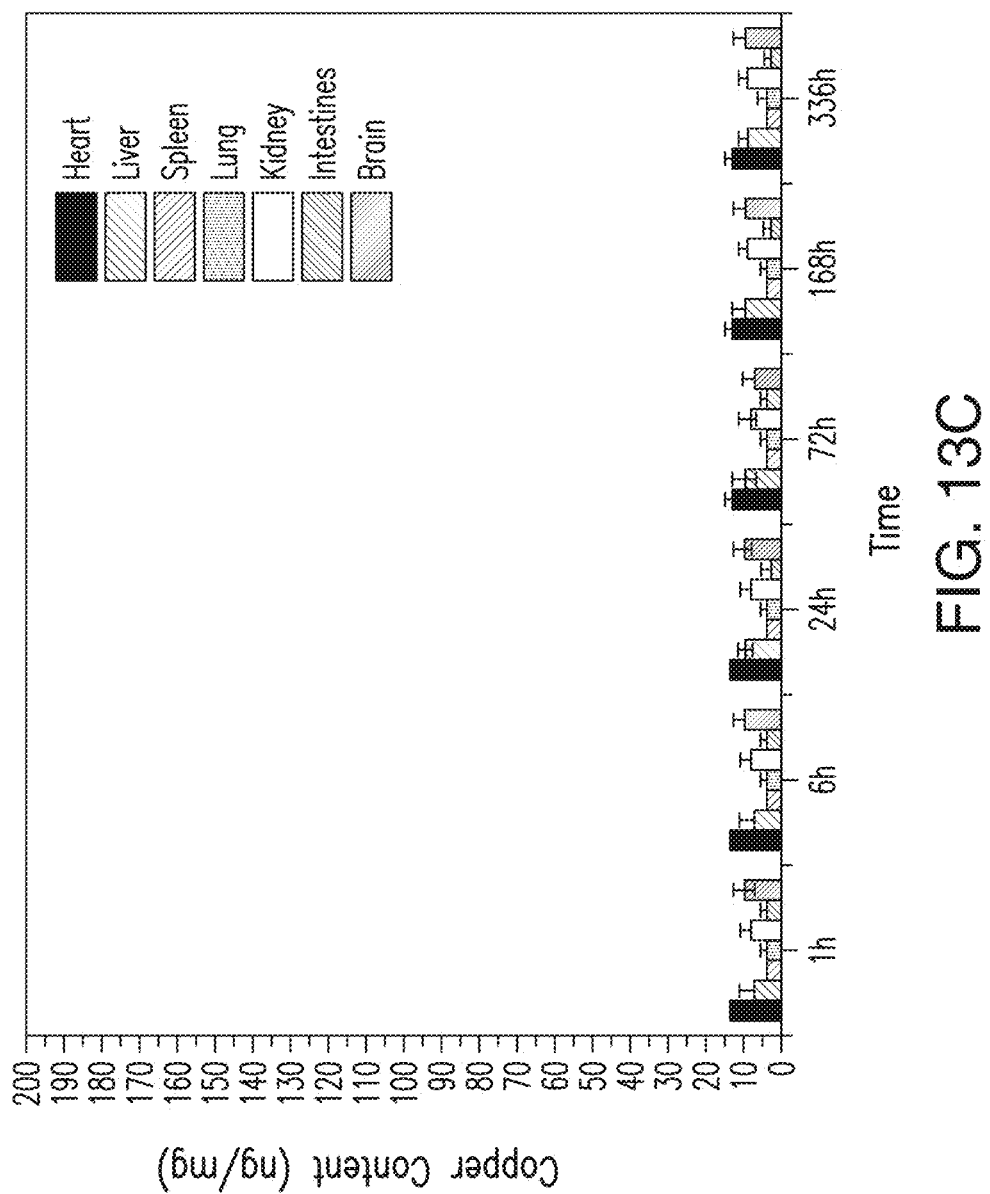

As shown in FIG. 13, the biodistribution of Cu-Cy nanoparticles was measured in the main organs (heart, liver, spleen, lung, kidney, brain, intestines), and it was found that the nanoparticles were mainly distributed in lung and liver. After 72 hours, the high dose group and low dose group were completely back to the approximately normal levels.

Figure 14A:
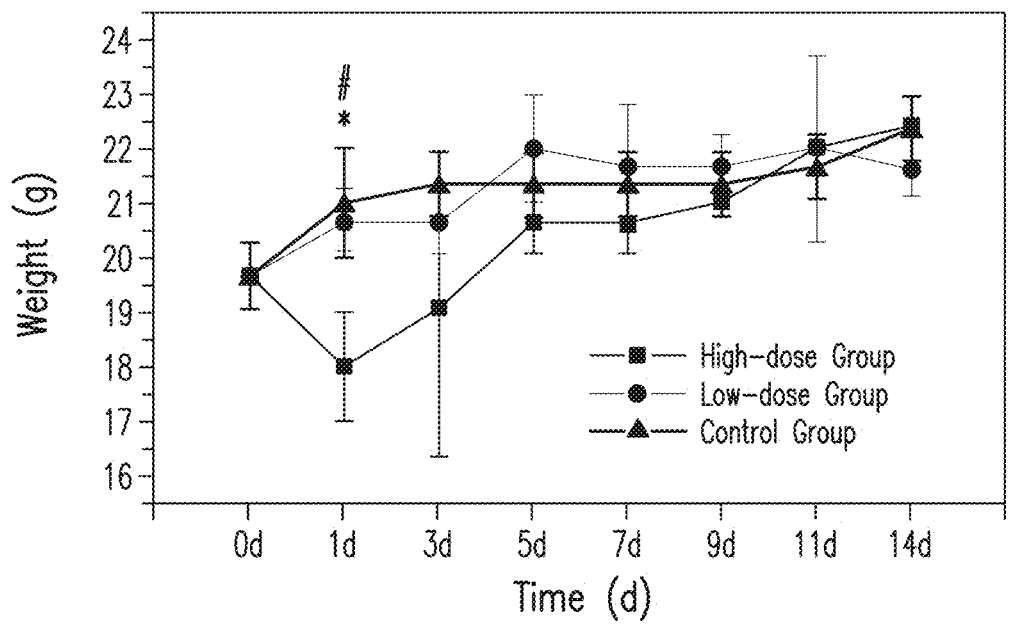
FIGS. 14A-14D show the change in animal weight (FIG. 14A), copper content in the blood (FIG. 14B), the copper content in the urine (FIG. 14C) and feces (FIG. 14D) over 14 days for control, 6.25m/mL (low dose) and 25 µg/mL (high dose).
Figure 14B:
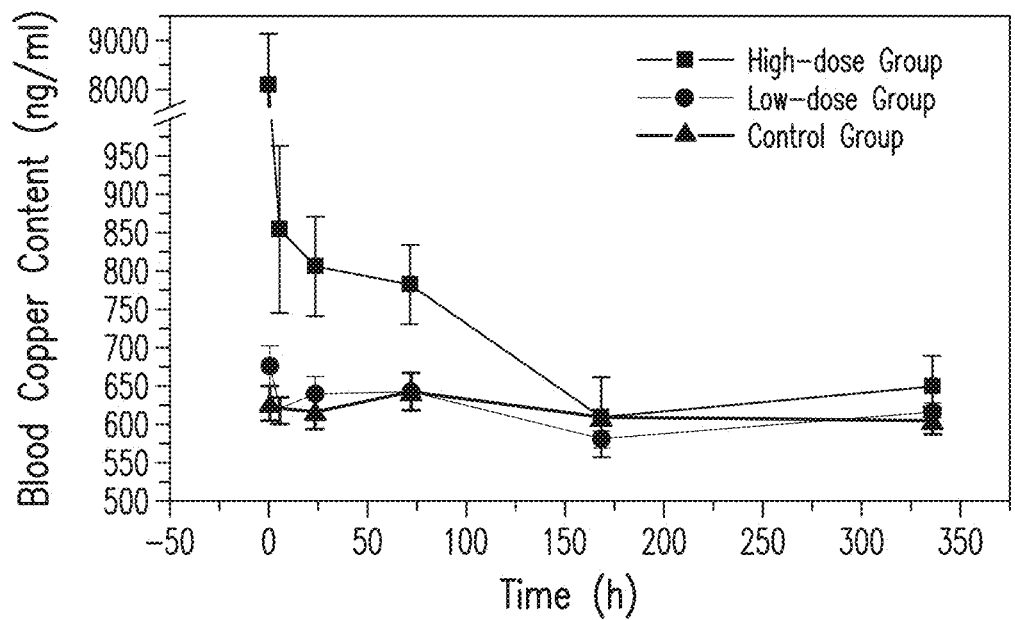
Figure 14C:
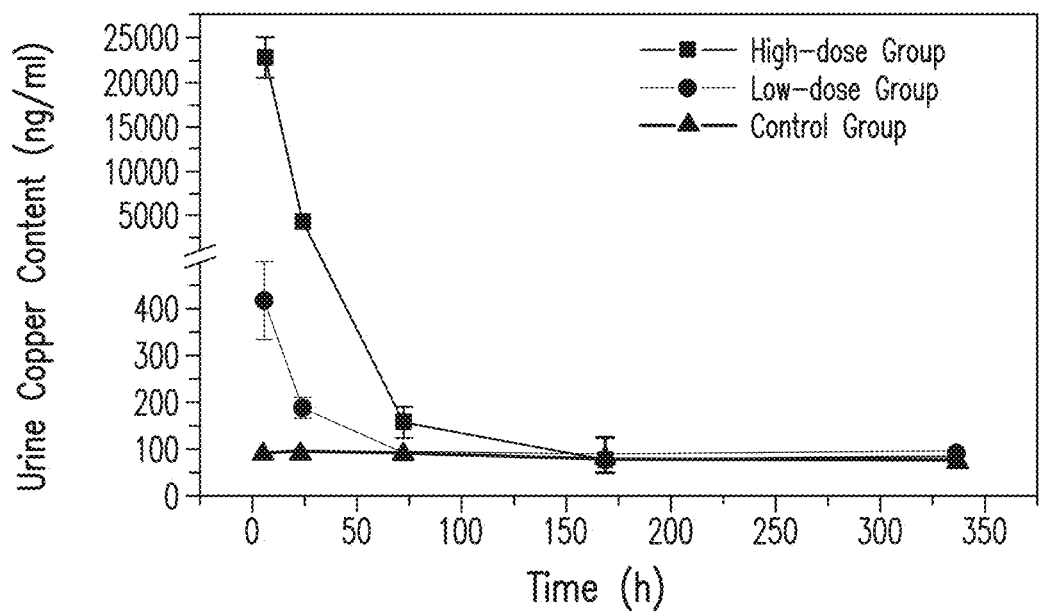
Figure 14D:
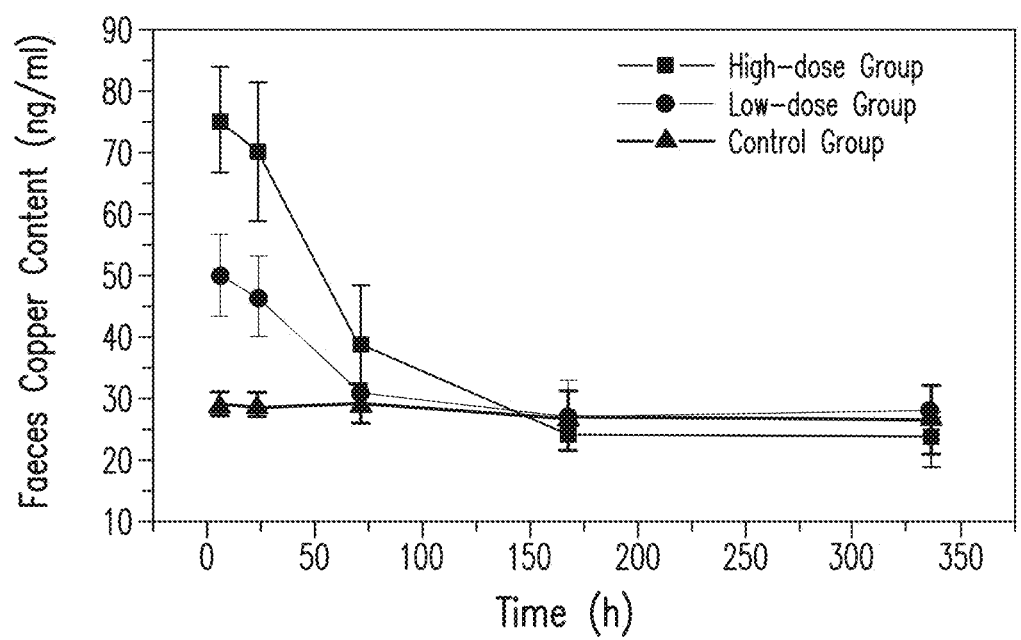

Particle Clearance 120 female Balb/c mice (20-25 g, 5 weeks) were injected intravenously with Cu-Cy nanoparticles in 3 groups randomly-high dose group (100 mg/kg), which was 20 times higher than cure dose; low dose group (5 mg/kg, the treat dose); and control group. The mice (n=3) were euthanized at different time points (1 hour, 6 hours, 24 hours, 72 hours, 168 hours and 336 hours). The blood, urine, feces, and parts of the major organs (brain, heart, liver, spleen, lung kidney) were collected and dissolved with 2 mL $HNO_3$ and HCl (v/v=1:3), and then heated at 70° C. for 5 min to obtain clear solutions. After that, the solutions were centrifuged at 3000 rpm for 10 min and the supernatants were kept for further inductively coupled plasma mass spectrometry (ICP-MS) analysis. Parts of the major organs (heart, liver, spleen, lung, kidney, brain intestines) were dehydrated using buffered formalin, ethanol with different concentrations, and xylene. They were then embedded in liquid paraffin. The sliced organs (3-5 mm) were stained with hematoxylin and eosin (H&E) and examined by a microscope (Olympus, BX51). As shown in FIGS. 14A-14D the metabolic activity of copper was greatest within the first 3 days through blood and urine. As seen in FIG. 14C copper was observed to be excreted from the body with urine.

In Vivo Toxicity

Figure 15:
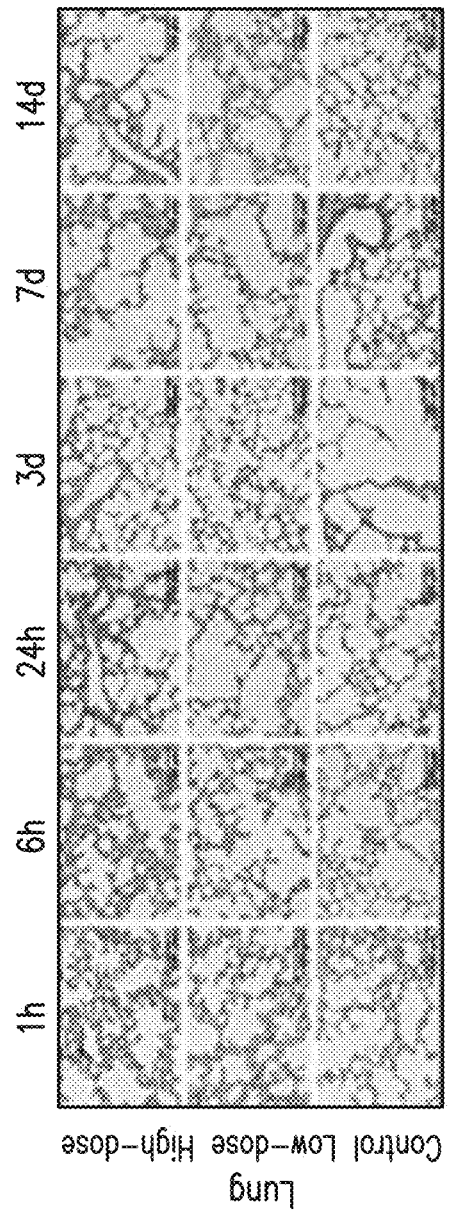
FIG. 15 shows the H&E staining for copper content in the lungs over days 1-14 for Balb/c mice in control, low dose and high dose groups, respectively.
Figure 16:
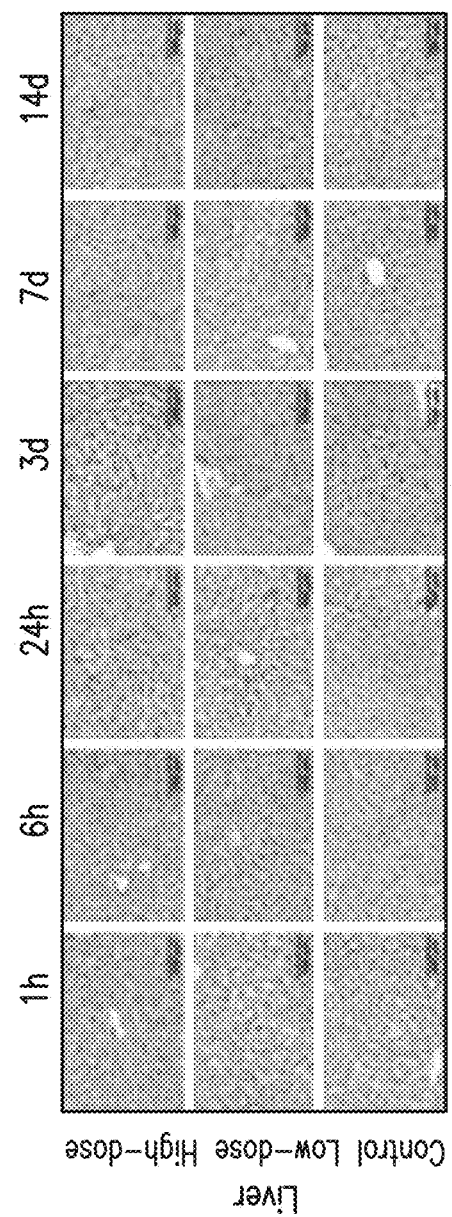
FIG. 16 shows the H&E staining for copper content in the liver over days 1-14 for Balb/c mice in control, low dose and high dose groups, respectively.
Figure 17:
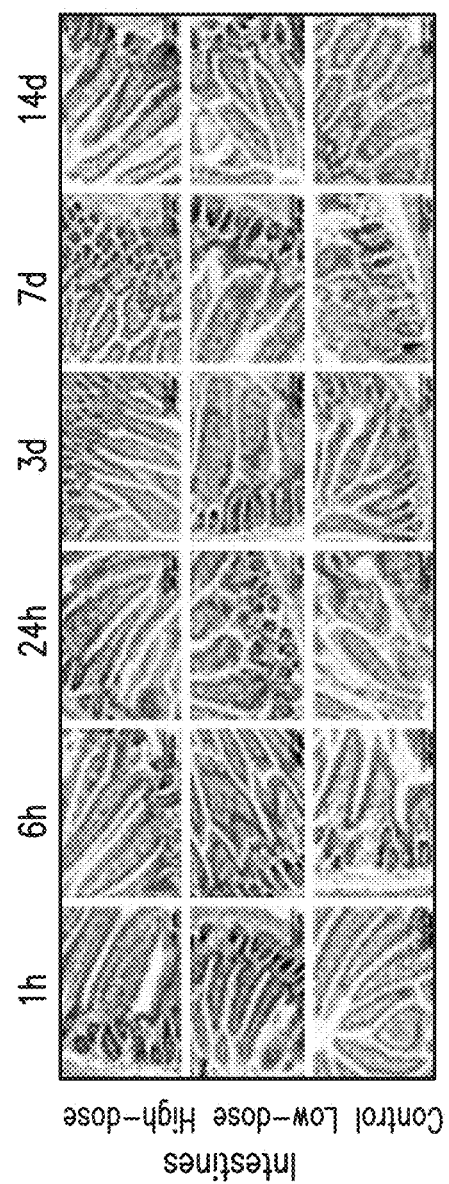
FIG. 17 shows the H&E staining for copper content in the intestines over days 1-14 for Balb/c mice in control, low dose and high dose groups, respectively.

FIGS. 15, 16 and 17 depict the H&E staining of tissue derived respectively from the lung, liver and intestines of animals in the control group, the low dose group (6.25 μg/mL) and the high dose group (25 μg/mL) over 14 days.

There was mild pulmonary congestion and moderate swallowed particles found in the lung. This phenomenon disappeared at 24 hours, there was no difference between the 3 organ groups after 72 hours. The results display no difference between the low dose group and control group, which indicates that the Cu-Cy is nontoxic at these doses. As seen in FIG. 15, FIG. 16 and FIG. 17, there was no difference between the low dose group and control group, which indicates the safety of Cu-Cy in treatment dose.

As seen in FIG. 15, FIG. 16 and FIG. 17, there was slight hepatocyte cell swelling at 1 and 6 hours. Then, the hepatocyte cells became normoxic at 24 hours and displayed no difference from low dose group and control group. No swelling cells were observed within the low dose group along with no significant differences from control group. Furthermore, there were no fragment or necrosis cells in all groups. The results showed that high dose treatments can induce hepatocyte cell swelling for a short period, then the hepatocyte cells can recover over a period of time.

We also investigated the H&E images of heart, spleen, kidney, intestines, and brain as shown in the supplementary Figures S3-S6 and found no difference from the high dose group, low dose group, and the control group. The cells of all these tissues were in normal structure and showed no obvious toxicity.

These results indicate that Cu-Cy is a safe medicine with a good biocompatibility and low toxicity. The metabolic activity of copper was highly concentrated within the first 3 days through blood and urine. The most effective metabolic pathway may be considered the injection of the copper nanoparticles directly into the blood circulation, in which they will flow through the liver and kidney and be excreted from the body with urine.

Figure 18:
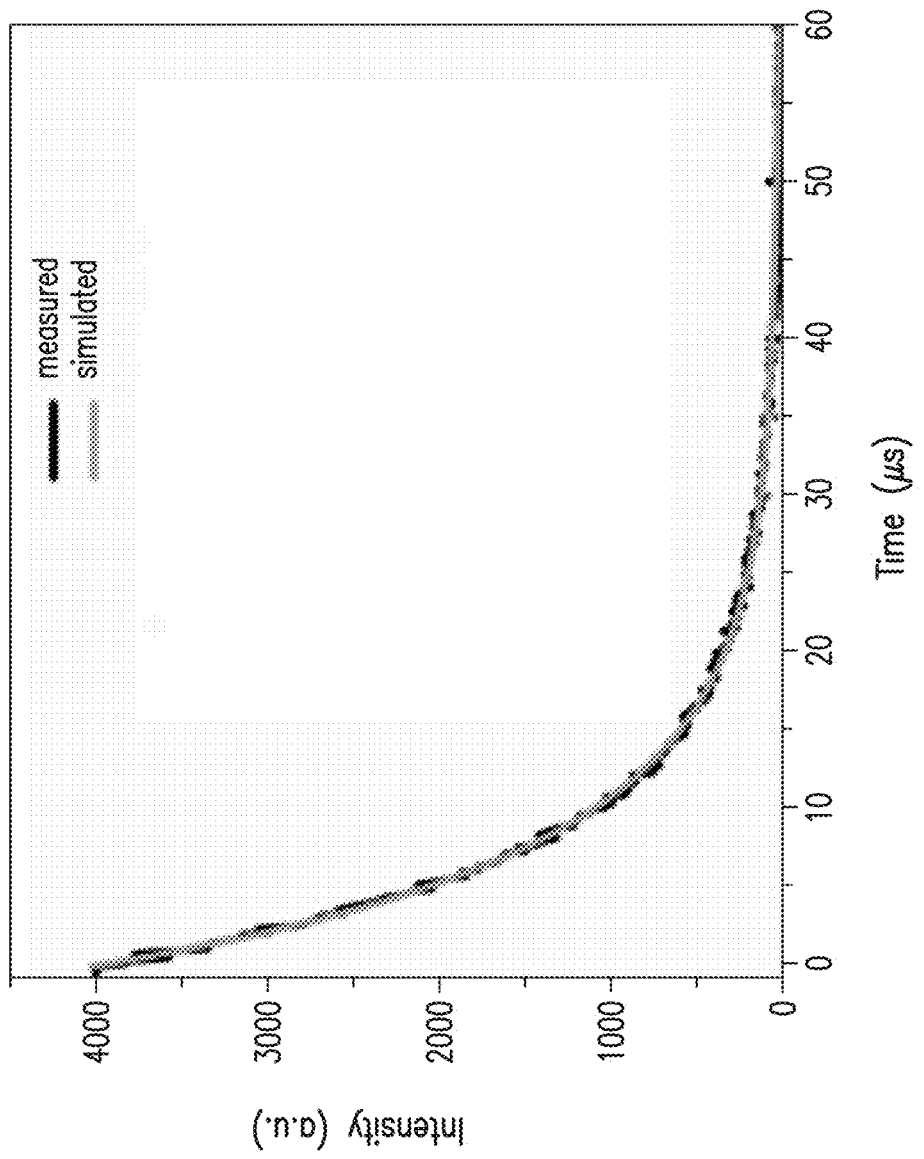
FIG. 18 shows the complete overlap of the theoretical luminescence decay curve and the observed emission spectrum when Cu-Cy is excited at 360 nm and monitored at 625 nm.

FIG. 18 depicts the complete overlap of the theoretical luminescence decay curve and the observed emission spectrum when Cu-Cy is excited at 360 nm and monitored at 625 nm. Cu-Cy nanoparticles have two sufficiently long decays—one is 7.399 microseconds and the slower one is 0.363 milliseconds—which are in the same range of luminescence decay lifetimes from triplet states of photosensitizers and other organic compounds. This means that Cu-Cy nanoparticles have long-lived triplet states that are required for energy transfer to the ground state triplet oxygen to produce singlet oxygen. These results are summarized below in Table II.

TABLE II

| Model Equation | ExpDec2 $Y = A1^{(-x/t1)} + A2^{(-x/t2)} + y^0$ | | |
|---|---|---|---|
| Reduced Chi-sqr. | 687.4205 | Excitation 360 nm | Emission 625 nm |
| Adj. R-square | 0.99911 | Value | |
| B | $y^0$ | −565.15059 | |
| B | A1 | 3910.58511 | |
| B | t1 | 7.39908 | |
| B | A2 | 580.79416 | |
| B | t2 | 363.47019 | |
| B | k1 | 0.13515 | |
| B | k2 | 0.00275 | |
| B | tau1 | 5.12865 | |
| B | tau2 | 251.193834 | |

Figure 19:
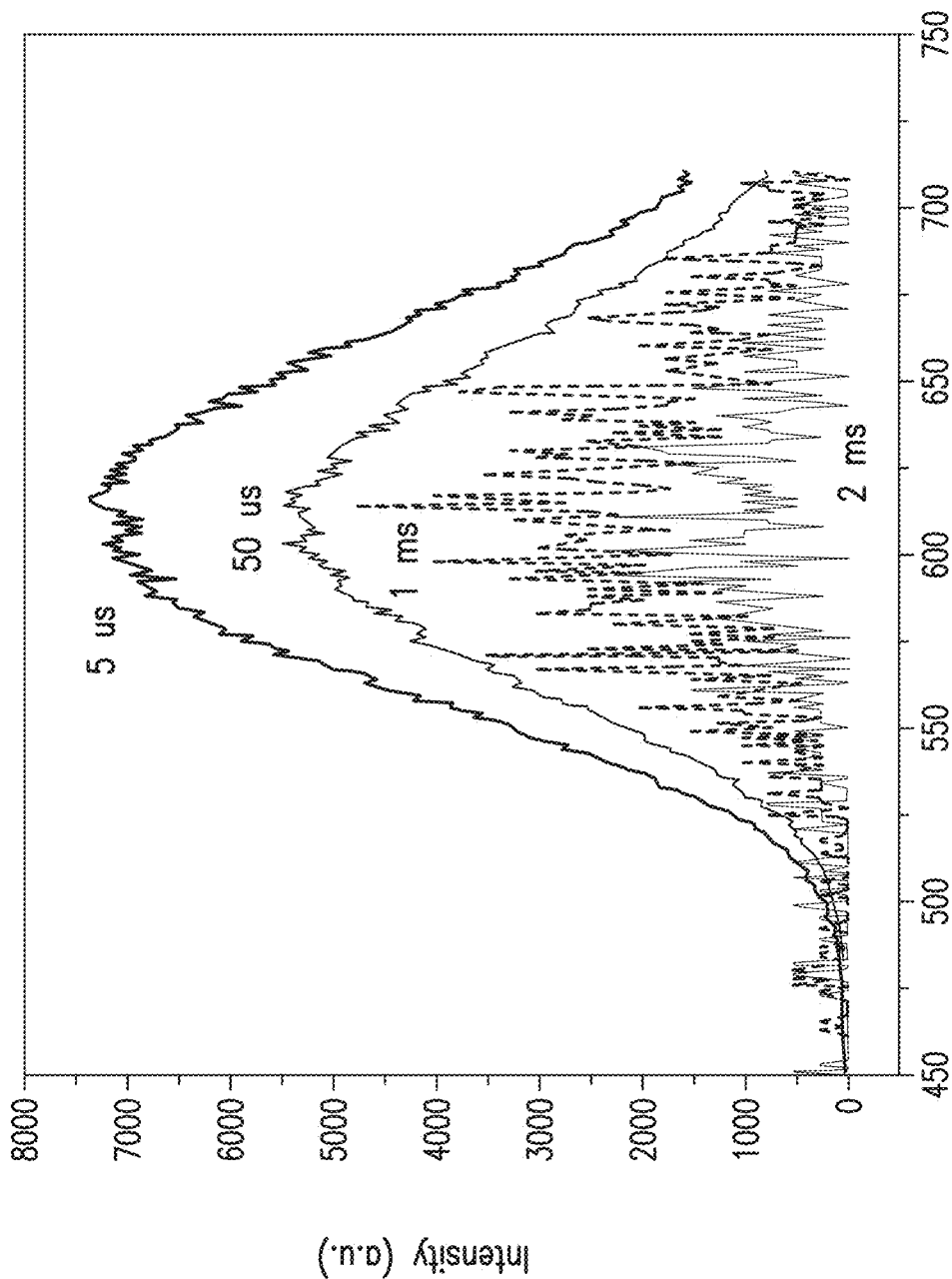
FIG. 19 depicts the time-gated emission spectra of a Cu-Cy nanoparticle aqueous solution at 5 µs, 50 µs, 1 ms and 2 ms.

FIG. 19 depicts the time-gated emission spectra of a Cu-Cy nanoparticle aqueous solution at 5 μs, 50 μs, 1 ms and 2 ms.

Figure 24:
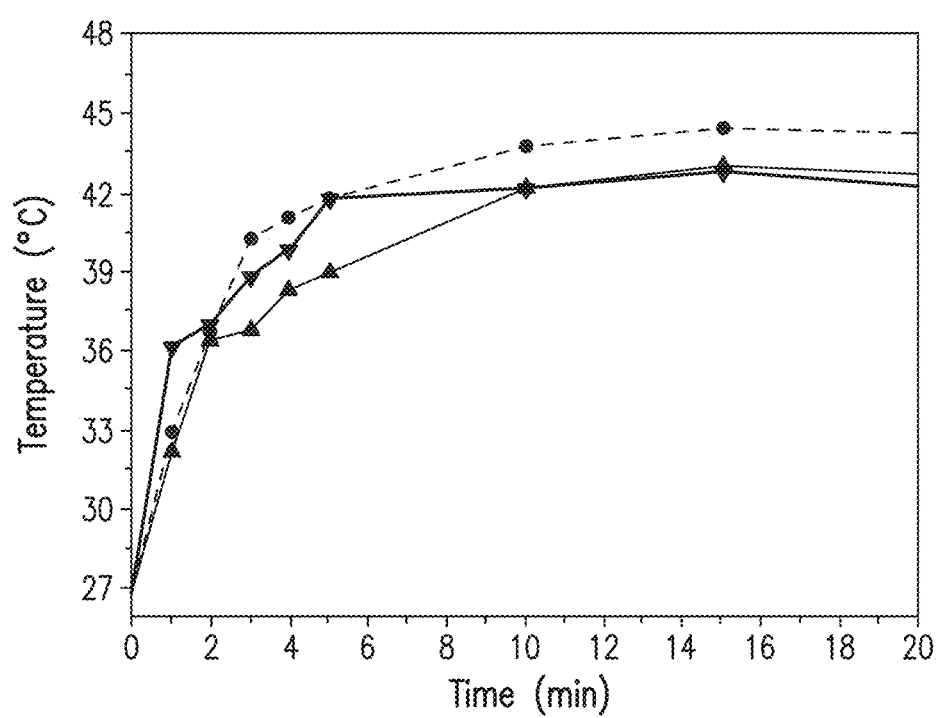
FIG. 24 depicts the microwave induced heating of water (●), a 0.5 mg/mL solution of Cu-Cy (▲), and a 1.5 mg/mL solution of Cu-Cy (▼).
Figure 25:
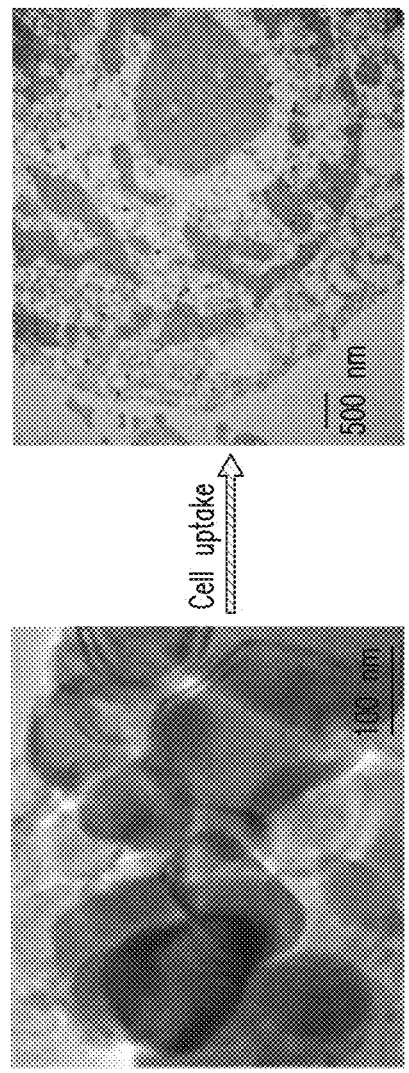
FIG. 25 depicts the TEM images of Cu-Cy particles for the original particles (left) and particles after uptake by osteosarcoma cells (right).

FIG. 24 depicts the microwave induced heating of water (■), a 0.5 mg/mL solution of Cu-Cy (▲), and a 1.5 mg/mL solution of Cu-Cy (▼). Without wishing to be limited by theory, as depicted in FIG. 24, the temperatures in Cu-Cy nanoparticle aqueous solutions are a little lower than in DI water. As such, it is observed that Cu-Cys nanoparticle solutions have better microwave absorption than water, but the absorbed energy is used for singlet oxygen production rather than for heating, so the photodynamic therapy effect is more effective than general heating in this case. This also can be seen from the change of the cell shape before and after the treatment. If the cell death is caused by heating, the cells would be expected to become more rounded in shape, possibly as a result of the condensation of skeletal proteins. As seen in FIG. 2, the cell shapes are almost the same before and after treatment. As such, hypothermia by heating does not appear to be a cause of cell death. As the microwave power or energy increases, both the heating temperature and the singlet oxygen production increases, therefore, the heating (hypothermia) and the photodynamic therapy complement one another.

Compositions

Disclosed herein are compositions for the treatment of cancer or for treating a disease that is susceptible to attack by reactive oxygen species. One aspect of the disclosed compositions comprises:

a) copper cysteamine nanoparticles having the formula:

b) a pharmaceutically acceptable carrier.

The disclosed methods include administration of the disclosed compounds in combination with a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical formulation in which it is contained. The carrier would naturally be selected to minimize any degradation of the active ingredient and to minimize any adverse side effects in the subject, as would be well known to one of skill in the art. In another aspect, many of the disclosed compounds can be used prophylactically, i.e., as a preventative agent, either neat or with a pharmaceutically acceptable carrier. The ionic liquid compositions disclosed herein can be conveniently formulated into pharmaceutical compositions composed of neat ionic liquid or in association with a pharmaceutically acceptable carrier. See e.g., *Remington's Pharmaceutical Sciences*, latest edition, by E.W. Martin Mack Pub. Co., Easton, Pa., which discloses typical carriers and conventional methods of preparing pharmaceutical compositions that can be used in conjunction with the preparation of formulations of the compounds described herein and which is incorporated by reference herein. Such pharmaceutical carriers, most typically, would be standard carriers for administration of compositions to humans and non-humans, including solutions such as sterile water. Other compounds can be administered according to standard procedures used by those skilled in the art. For example, pharmaceutical compositions can also include one or more additional active ingredients such as antimicrobial agents, anti-inflammatory agents, anesthetics, and the like.

Examples of pharmaceutically-acceptable carriers include, but are not limited to, saline, Ringer's solution and dextrose solution. Further carriers include sustained release preparations such as semipermeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Methods

Disclosed herein are methods for the treatment of cancer. Stated another way, disclosed herein are methods for kill targeted cells. As such, the targeted cells are not necessarily cancer or tumor cells, but cells which the formulator wished to kill. In general, the disclosed photodynamic therapy relates to contacting cancer cells, whether in the form of a solid defined tumor mass or not, with a composition comprising the disclosed copper cysteamine nanoparticles. Once the target cells have taken up the copper-cysteamine nanoparticles, the cells are irradiated using microwave radiation. The source of microwave radiation can be any source sufficient to achieve activation of the nanoparticles. Activation of the nanoparticles produces reactive oxygen species, inter alia, hydroxyl radicals (.OH), singlet oxygen ($^1O_2$), peroxides (R—O—O.) and the like.

In one aspect disclosed herein is a photodynamic therapy for treating cancer, comprising:
a) contacting cancer cells with copper-cysteamine; and
b) exposing the copper-cysteamine to a source of microwave radiation.

In another aspect disclosed herein are methods for treating cancer, comprising:
a) contacting cancer cells with a composition comprising from about 0.5 mg/mL to about 250 mg/mL of copper cysteamine nanoparticles having the formula:

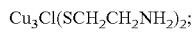
$Cu_3Cl(SCH_2CH_2NH_2)_2$;

wherein the nanoparticles are absorbed by the cancer cells; and
b) irradiating the cancer cells comprising the copper cysteamine nanoparticles.

A further aspect disclosed herein are methods for forming a reactive oxygen species in a targeted cell in a subject, comprising:
a) contacting the targeted cells with copper-cysteamine; and
b) exposing the targeted cells containing copper-cysteamine to a source of microwave radiation.

The targeted cells, i.e., cancer cells or tumor can be contacted with an aqueous solution comprising from about 0.5 μg/mL to about 250 μg/mL. In one embodiment the compositions can comprise from about 1 μg/mL to about 100 μg/mL. In another embodiment the compositions can comprise from about 10 μg/mL to about 100 μg/mL. In a further embodiment the compositions can comprise from about 5 μg/mL to about 20 μg/mL. In a yet further embodiment the compositions can comprise from about 1 μg/mL to about 50 μg/mL. In a yet another embodiment the compositions can comprise from about 1 μg/mL to about 10 μg/mL. In a still further embodiment the compositions can comprise from about 15 μg/mL to about 50 μg/mL. In still another embodiment the compositions can comprise from about 20 μg/mL to about 200 μg/mL.

The compositions can comprise any amount of the disclosed cysteamine nanoparticles from about 0.5 μg/mL to about 250 μg/mL, for example, 1 μg/mL, 2 μg/mL, 3 μg/mL, 4 μg/mL, 5 μg/mL, 6 μg/mL, 7 μg/mL, 8 μg/mL, 9 μg/ml, 10 μg/ml, 11 μg/mL, 12 μg/mL, 13 μg/mL, 14 μg/mL, 15 μg/mL, 16 μg/mL, 17 μg/mL, 18 μg/mL, 19 μg/ml, 20 μg/ml, 22 μg/mL, 22 μg/mL, 23 μg/mL, 24 μg/mL, 25 μg/mL, 26 μg/mL, 27 μg/mL, 28 μg/mL, 29 μg/ml, 30 μg/mL, 31 μg/mL, 32 μg/mL, 33 μg/mL, 34 μg/mL, 35 μg/mL, 36 μg/mL, 37 μg/mL, 38 μg/mL, 39 μg/mL, 40 μg/mL, 41 μg/mL, 42 μg/mL, 43 μg/mL, 44 μg/mL, 45 μg/mL, 46 μg/mL, 47 μg/mL, 48 μg/mL, 49 μg/mL, 50 μg/mL, 51 μg/mL, 52 μg/mL, 53 μg/mL, 54 μg/mL, 55 μg/mL, 56 μg/mL, 57 μg/mL, 58 μg/mL, 59 μg/mL, 60 μg/mL, 61 μg/mL, 62 μg/mL, 63 μg/mL, 64 μg/mL, 65 μg/mL, 66 μg/mL, 67 μg/mL, 68 μg/mL, 69 μg/mL, 70 μg/mL, 71 μg/mL, 72 μg/mL, 73 μg/mL, 74 μg/mL, 75 μg/mL, 76 μg/mL, 77 μg/mL, 78 μg/mL, 79 μg/mL, 80 μg/mL, 81 μg/mL, 82 μg/mL, 83 μg/mL, 84 μg/mL, 85 μg/mL, 86 μg/mL, 87 μg/mL, 88 μg/mL, 89 μg/mL, 90 μg/mL, 91 μg/mL, 92 μg/mL, 93 μg/mL, 94 μg/mL, 95 μg/mL, 96 μg/mL, 97 μg/mL, 98 μg/mL, 99 μg/mL and 100 μg/mL.

The formulator can deliver the desired amount of Cu-Cy nanoparticle in any manner desired. For example, if a bolus of 30 μg of nanoparticle is desirable, the formulator can deliver 1 mL of a solution comprising 30 μg/mL or 0.3 mL of a solution comprising 100 μg/mL.

The copper cysteamine nanoparticles can have any average size from about 0.5 nanometers to about 100 nanometers. In one embodiment the copper cysteamine nanoparticles can have an average particle size of from about 1 nm to about 50 nm. In another embodiment the copper cysteamine nanoparticles can have an average particle size of from about 5 nm to about 25 nm. In a further embodiment the copper cysteamine nanoparticles can have an average particle size of from about 10 nm to about 20 nm. In a yet further embodiment the copper cysteamine nanoparticles can have an average particle size of from about 5 nm to about 20 nm. In a yet another embodiment the copper cysteamine nanoparticles can have an average particle size of from about 0.5 nm to about 5 nm. In a still yet further embodiment the copper cysteamine nanoparticles can have an average particle size of from about 12 nm to about 17 nm.

The disclosed compositions can comprise copper cysteamine nanoparticles having any average size from about 0.5 nanometers to about 100 nanometers, for example, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 22 nm, 22 nm, 23 nm, 24 nm, 25 nm, 26 nm, 27 nm, 28 nm, 29 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm, 81 nm, 82 nm, 83 nm, 84 nm, 85 nm, 86 nm, 87 nm, 88 nm, 89 nm, 90 nm, 91 nm, 92 nm, 93 nm, 94 nm, 95 nm, 96 nm, 97 nm, 98 nm, 99 nm and 100 nm.

The power level of the microwave radiation used in the disclosed therapies can be any power decided by the user. For example, from about 0.5 watts to about 100 W. The microwave power can be any amount from 0.5 W to 100 W, for example, 1 W, 2 W, 3 W, 4 W, 5 W, 6 W, 7 W, 8 W, 9 W, 10 W, 11 W, 12 W, 13 W, 14 W, 15 W, 16 W, 17 W, 18 W, 19 W, 20 W, 22 W, 22 W, 23 W, 24 W, 25 W, 26 W, 27 W, 28 W, 29 W, 31 W, 32 W, 33 W, 34 W, 35 W, 36 W, 37 W, 38 W, 39 W, 40 W, 41 W, 42 W, 43 W, 44 W, 45 W, 46 W, 47 W, 48 W, 49 W, 50 W, 51 W, 52 W, 53 W, 54 W, 55 W, 56 W, 57 W, 58 W, 59 W, 60 W, 61 W, 62 W, 63 W, 64 W, 65 W, 66 W, 67 W, 68 W, 69 W, 70 W, 71 W, 72 W, 73 W, 74 W, 75 W, 76 W, 77 W, 78 W, 79 W, 80 W, 81 W, 82 W, 83 W, 84 W, 85 W, 86 W, 87 W, 88 W, 89 W, 90 W, 91 W, 92 W, 93 W, 94 W, 95 W, 96 W, 97 W, 98 W, 99 W and 100 W.

The duration of exposure, i.e., the amount of time that the radiation is applied to the cells containing the Cu-Cy nanoparticles can be determined by the user of the disclosed photodynamic therapy. For example, 1 sec., 2 sec., 3 sec., 4 sec., 5 sec., 6 sec., 7 sec., 8 sec., 9 sec., 10 sec., 11 sec., 12 sec., 13 sec., 14 sec., 15 sec., 16 sec., 17 sec., 18 sec., 19 sec., 20 sec., 22 sec., 22 sec., 23 sec., 24 sec., 25 sec., 26 sec., 27 sec., 28 sec., 29 sec., 31 sec., 32 sec., 33 sec., 34 sec., 35 sec., 36 sec., 37 sec., 38 sec., 39 sec., 40 sec., 41 sec., 42 sec., 43 sec., 44 sec., 45 sec., 46 sec., 47 sec., 48 sec., 49 sec., 50 sec., 51 sec., 52 sec., 53 sec., 54 sec., 55 sec., 56 sec., 57 sec., 58 sec., 59 sec., 60 sec., 61 sec., 62 sec., 63 sec., 64 sec., 65 sec., 66 sec., 67 sec., 68 sec., 69 sec., 70 sec., 71 sec., 72 sec., 73 sec., 74 sec., 75 sec., 76 sec., 77 sec., 78 sec., 79 sec., 80 sec., 81 sec., 82 sec., 83 sec., 84 sec., 85 sec., 86 sec., 87 sec., 88 sec., 89 sec., 90 sec., 91 sec., 92 sec., 93 sec., 94 sec., 95 sec., 96 sec., 97 sec., 98 sec., 99 sec. and 100 sec.

The microwave radiation can be applied continuously or the radiation can be pulsed. Therefore, the application format, time and power level can be adjusted by the user to meet the needs of the patient having cancer.

The following are non-limiting examples of cancers that can be treated by the disclosed methods and compositions: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytoma/Malignant Glioma; Craniopharyngioma; Ependymoblastoma; Ependymoma; Medulloblastoma; Medulloepithelioma; Pineal Parenchymal Tumors of Intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma; Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; Intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocytoma of Bone and Osteosarcoma; Medulloblastoma; Melanoma; Melanoma, Intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Cell Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sézary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenström Macroglobulinemia; and Wilms Tumor.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method for producing a reactive oxygen species in selected cells in vivo, comprising:
   a) administering a composition comprising copper-cysteamine (Cu-Cy) nanoparticles having the formula:

$Cu_3Cl(SCH_2CH_2NH_2)_2$;

to selected cells in a subject; and
   b) exposing the copper-cysteamine to a source of microwave radiation.

2. The method according claim 1, wherein the composition comprises from about 1 µg/mL to about 100 µg/mL of the copper cysteamine nanoparticles.

3. The method according to claim 1, wherein the average particle size of the Cu-Cy nanoparticle is from about 0.5 nm to about 100 nm.

4. The method according to claim 1, wherein the composition comprises from about 10 µg/mL to about 100 µg/mL of the copper cysteamine nanoparticles.

5. The method according to claim 1, wherein the composition comprises from about 5 µg/mL to about 20 µg/mL of the copper cysteamine nanoparticles.

6. The method according to claim 1, wherein the composition comprises from about 1 µg/mL to about 50 µg/mL of the copper cysteamine nanoparticles.

7. The method according to claim 4, wherein the average particle size of the Cu-Cy nanoparticle is from about 0.5 nm to about 100 nm.

* * * * *